(12) United States Patent
Gryskiewicz et al.

(10) Patent No.: US 11,918,455 B2
(45) Date of Patent: Mar. 5, 2024

(54) METHODS AND SYSTEMS FOR DELIVERING A FILLED PROSTHETIC BLADDER INTO A SURGICAL CAVITY

(71) Applicant: Dr. Joe Gryskiewicz L.L.C., Burnsville, MN (US)

(72) Inventors: Joseph M. Gryskiewicz, Edina, MN (US); James A. Peterson, Edina, MN (US)

(73) Assignee: DR. JOE GRYSKIEWICZ, L.L.C., Burnsville, MN (US)

( * ) Notice: Subject to any disclaimer, the term of this patent is extended or adjusted under 35 U.S.C. 154(b) by 382 days.

(21) Appl. No.: 17/393,390

(22) Filed: Aug. 3, 2021

(65) Prior Publication Data

US 2022/0054254 A1 Feb. 24, 2022

Related U.S. Application Data

(63) Continuation of application No. 17/047,658, filed as application No. PCT/US2019/052898 on Sep. 25, 2019, now Pat. No. 11,083,564.

(Continued)

(51) Int. Cl.
*A61F 2/12* (2006.01)

(52) U.S. Cl.
CPC ........ *A61F 2/12* (2013.01); *A61F 2210/0014* (2013.01); *A61F 2220/005* (2013.01); *A61F 2220/0083* (2013.01); *A61F 2230/0023* (2013.01); *A61F 2250/0019* (2013.01); *A61F 2250/0021* (2013.01); *A61F 2250/0097* (2013.01)

(58) Field of Classification Search
CPC ................ A61F 2/12; A61F 2210/0014; A61F 2220/005; A61F 2220/0083; A61F 2230/0023; A61F 2250/0019; A61F 2250/0021; A61F 2250/0097
IPC .......................................... A61F 2/12
See application file for complete search history.

(56) References Cited

U.S. PATENT DOCUMENTS 2,957,510 A 10/1960 Moser
7,491,227 B2 * 2/2009 Yang ......................... A61F 2/91
623/1.15

(Continued)

FOREIGN PATENT DOCUMENTS

WO WO 2018/162345 A1 9/2018

OTHER PUBLICATIONS

PCT International Search Report for PCT/US2019/052898, dated Dec. 27, 2019, 2 pages.

(Continued)

*Primary Examiner* — Suzette J Gherbi
(74) *Attorney, Agent, or Firm* — Husch Blackwell LLP

(57) ABSTRACT

A prosthetic insertion apparatus and related methods of use in delivering filled prosthetic bladders through a skin incision and into a surgical cavity or pocket. The prosthetic insertion apparatus imparts control and retention properties to a surgical professional such the prosthetic bladder can be oriented and manipulated into the surgical cavity without risk of inadvertent dropping of the prosthetic bladder and without imparting damaging stress or torque to the bladder. Suitable materials can be utilized that are selected as having advantageous properties including lubricity, rigidity, easily sterilizable, and high strength.

15 Claims, 23 Drawing Sheets

Related U.S. Application Data

(60) Provisional application No. 62/736,271, filed on Sep. 25, 2018.

(56) References Cited

U.S. PATENT DOCUMENTS

| | | | |
|---|---|---|---|
| 10,004,534 B2* | 6/2018 | Anderson | A61B 17/3468 |
| 11,083,564 B2* | 8/2021 | Gryskiewicz | A61F 2/12 |
| 2007/0038310 A1* | 2/2007 | Guetty | A61F 2/0059 |
| | | | 623/23.72 |
| 2012/0259414 A1 | 10/2012 | Preissman | |
| 2015/0032208 A1* | 1/2015 | Preissman | A61F 2/12 |
| | | | 623/8 |
| 2016/0374720 A1* | 12/2016 | Anderson | A61F 2/0095 |
| | | | 623/8 |
| 2017/0181841 A1* | 6/2017 | Weinzweig | A61B 17/3468 |
| 2018/0116779 A1 | 5/2018 | Marx | |
| 2018/0168790 A1 | 6/2018 | Rosenberg | |
| 2019/0175331 A1* | 6/2019 | Horndeski | A61F 2/0077 |
| 2020/0008921 A1* | 1/2020 | Alden | A01N 1/0273 |
| 2020/0008923 A1* | 1/2020 | Geiger | A61B 17/3431 |
| 2023/0293299 A1* | 9/2023 | Khairkhahan | A61F 2/2466 |
| | | | 623/2.11 |

OTHER PUBLICATIONS

PCT Written Opinion of the ISA for PCT/US2019/052898, dated Dec. 27, 2019, 7 pages.
European Supplementary Search Report for Application No. 19 86 7556, dated May 13, 2022, 2 pages.
Application and File history for U.S. Appl. No. 17/047,658, filed Oct. 14, 2020. Inventors: Joseph M. Gryskiewicz et al.

* cited by examiner

METHODS AND SYSTEMS FOR DELIVERING A FILLED PROSTHETIC BLADDER INTO A SURGICAL CAVITY

CROSS-REFERENCE TO RELATED APPLICATIONS

The present application is a continuation application of U.S. patent application Ser. No. 17/047,658, filed on Oct. 14, 2020 and issuing on Aug. 10, 2021 as U.S. Pat. No. 11,083,564, which was a National Phase entry of PCT Application No. PCT/US2019/052898, filed on Sep. 25, 2019, which claims priority to U.S. Provisional Application Ser. No. 62/736,271 filed Sep. 25, 2018 and entitled "METHODS AND SYSTEMS FOR DELIVERING A FILLED PROSTHETIC BLADDER INTO A SURGICAL CAVITY", all of which are hereby incorporated by reference in their entirety.

TECHNICAL FIELD

The present disclosure relates generally to methods and systems for delivering a filled prosthetic bladder. More specifically, the present disclosure is directed to methods and systems for surgically inserting a prosthetic bladder, such as breast prostheses, through a skin and into a surgical cavity or pocket.

BACKGROUND

Breast augmentation surgery, or augmentation mammoplasty, is a surgical procedure that involves using breast implants or fat tissue transfers to increase the size of patients' breasts. Over the past decade, breast augmentation has become more common in the United States, and patients often seek augmentations to restore breast volume after weight loss or pregnancy, or to improve natural breast size and symmetry.

Most commonly, breast augmentation surgery involves inserting breast prostheses, or implants, into patients' breast cavities. Breast prostheses are bladder-like sacks that contain an outer membrane and an inner fluid; the inner fluid is often either saline or silicone. Conventionally, augmentations that use saline implants involve inserting an unfilled implant into a patient's breast cavity through a small incision; then, once the implant is in place in the cavity, the implant is filled with saline solution. Conversely, augmentations that use silicone implants involve inserting a prefilled silicone implant into a patient's breast cavity through a slightly larger incision.

While patients generally prefer the natural qualities of silicone implants, they are often apprehensive of the larger incisions and possibility of visible scars. Further, patients and physicians alike are frequently concerned with the longevity and integrity of silicone implants as a consequence of conventional insertion processes. Although several silicone implant insertion devices attempt to alleviate these concerns, existing devices exhibit several shortcomings. For example, existing insertion apparatuses are typically used under slippery conditions; these conditions are either induced intentionally to reduce frictional forces on the implant as it slides through the device, or unintentionally as a result of insertion apparatus preparation and implant transfer processes. Consequently, existing manual insertion methods and devices are often difficult to control and/or maintain in position, and silicone implants are difficult to insert precisely. In addition, in line with the surgical industries' concerns surrounding surgical suite sterility and contamination from skin bacteria resulting in early postoperative infection or painful, disfiguring capsular contracture months to years later, existing manual insertion techniques and devices raise concerns regarding the potential for cross-contamination as a result of apparatus preparation and implant transfer processes.

Due to the inability to control existing breast prostheses insertion devices, and concerns surrounding surgical suite cross-contamination associated with existing preparation and transfer processes, it would be advantageous to provide methods and systems for inserting a prosthetic bladder, such as breast prostheses, into a surgical cavity.

SUMMARY

The present disclosure is directed to prosthetic insertion apparatus and their related methods of use in delivering filled prosthetic bladders such as, for example, breast implants through a skin incision and into a surgical cavity or pocket. All of the various embodiments disclosed herein are capable of imparting control and retention properties to a surgical professional such the prosthetic bladder can be oriented and manipulated into the surgical cavity without risk of inadvertent dropping of the prosthetic bladder and without imparting damaging stress or torque to the bladder. In all of the various embodiments, suitable materials can be utilized that are selected as having advantageous properties such as, for example, lubricity, rigidity, easily sterilizable, and high strength. Generally, the various embodiments disclosed herein require no additional joining operations or tools such as, for example, adhesives, tapes, scissors, scalpels and the like, to successfully deliver the prosthetic bladder into the surgical cavity.

In one representative embodiment, a prostheses insertion device can comprise a delivery sheet that can accommodate any size/volume of prosthetic bladder. Generally, the surgical professional can lay the delivery sheet flat and fold the delivery sheet about the prosthetic bladder to facilitate control and precise delivery of the prosthetic bladder. The delivery sheet can be selected to have a delivery surface for example, by appropriate material selection or by applying a coating such that the delivery surface possesses lubricity and a low coefficient of friction such that the prosthetic bladder easily slides along the delivery surface without and binding. In some embodiments, the delivery surface can comprise a hydrophilic material that exhibits high lubricity when saline is applied to the delivery surface. In some embodiments, the delivery sheet can comprise an external surface that can include positioning indicia that provides a visible reference, for example, with respect to prosthetic bladder size/volume, to a surgical professional when folding and manipulating the delivery sheet about the prosthetic bladder. In some embodiments, the external surface can comprise one or more retention mechanism, for example, manipulation assisting divots, ribs, hook and loop fasteners and the like, to assist the surgical professional in maintaining the folded orientation about the prosthetic bladder during manipulation and delivery of the prosthetic bladder into the surgical cavity. In some embodiment, the delivery sheet can comprise a malleable or rigid guide that can be positioned in and through the incision such that a formed delivery orifice is maintained in proper relation to the incision as the surgical professional manipulates the prosthetic bladder through the delivery end and into the incision. In some embodiments, the malleable or rigid guide can include one or more tabs or a continuous lip that can be positioned within the surgical cavity and can interface with an inner wall of the surgical cavity to help retain the malleable or rigid guide within the incision. In one representative embodiment, the delivery sheet can be generally square in shape and any positioning indicia on the external surface can be centered on the sheet and aligned generally parallel to the sheet's lateral edges with the malleable or rigid guide centered on the delivery sheet's bottom edge. In another representative embodiment, the delivery sheet can be generally rhombus in shape with the positioning indicia being perpendicular relative to one another and aligned parallel to the delivery sheet's two bottom edges, and the malleable or rigid guide can be positioned proximate the delivery sheet's bottom corner.

In one aspect, the present disclosure is directed to a system for facilitating physician control and precise delivery of an implant into a surgical cavity through the use of a delivery sheet and an implant. In embodiments, the delivery sheet includes a surface that has a low coefficient of friction and includes indicia, a reverse surface that includes manipulation assisting divots, and an insertion tab. Further, the implant comprises a filled prostheses bladder.

In another aspect, the present disclosure is directed to a method of delivering a filled prostheses bladder into a surgical cavity. The method can comprise the step of removing the delivery sheet and prostheses from a package, and preparing the sheet for use. The method can further comprise the step of placing or otherwise positioning the prostheses on the delivery sheet. In some embodiments, the method can comprise the step of folding the delivery sheet around the delivery sheet and prostheses from a package, and preparing the sheet for use. The method can further comprise the step of placing or otherwise positioning the prostheses on the delivery sheet.

In some embodiments, the method can comprise the step of folding the delivery sheet around the prostheses. In other embodiments, the method can comprise the step of rolling the delivery sheet around the prostheses. The method can further comprise the step of using the insertion tab to guide manual manipulation of the sheet and prostheses in order to precisely deliver the prostheses into the surgical cavity.

In another aspect, a kit is provided. The kit can comprise a delivery sheet, a separate protective sheet to cover patient's skin and sequester any skin contaminants' and an implant. The delivery sheet of the kit includes a surface having a low coefficient of friction which can be coated with a lubricious agent and indicia, a reverse surface having manipulation assisting divots, and an insertion tab. The implant of the kit can include a filled prostheses bladder.

In another aspect, a prosthesis insertion device can comprise a receiving pocket having a closed end and an open insertion end. A bladder prosthesis be placed into the receiving pocket where a suitable lubrication or wetting agent can be applied. As the receiving pocket is closed and/or sealed, there is no risk of spilling the lubrication/wetting agent or having the prosthesis inadvertently fall out. The open insertion end is defined by a pair of opposed flaps that can be folded or rolled with respect to one another to selectively vary an insertion diameter/size of the open insertion end. In some embodiments, one or both of the flaps can include a means for retaining the flaps at the desired location relative to one another, for example, surface treatments to include friction, textures including for example, complimentary ribs or bumps that at least partially engage or even adhesives such that a surgical professional is assisted in maintaining the appropriate insertion diameter/size. In some embodiments, the open insertion end can include a stiff tab that assists with orienting the open insertion end relative to a surgical incision and that can be inserted through the surgical incision to assist with delivery the prosthesis into the surgical cavity. With the open insertion end positioned relative to the surgical incision, the surgical professional can manipulate, for example, by squeezing or rolling the material of the surgical pockets, to physically manipulate the prosthesis through the open insertion end and into the surgical cavity.

In another representative embodiment, a prosthesis insertion device can be fabricated from a bag formed of a polymeric material. Generally, the bag can be cut vertically from the open end toward a closed end. This vertical cut can be terminated prior to reaching the closed end. At this termination point, cuts can be made perpendicular to the vertical cut to form two opposed flaps positioned above the closed end. The surgical professional can position the bladder prosthesis into the closed end ant then wrap the two posed flaps around each other to form a conical delivery end having a delivery opening. In some embodiments, the bag can include a rigid or malleable guide at the open end so as to be part of the conical delivery end. The rigid or malleable guide can be insertable into a surgical incision and can include a lip or one or more tabs to retain the rigid or malleable guide within the surgical opening and to access the surgical cavity/pocket. The surgical professional can then squeeze or otherwise manipulate the closed end to bias the bladder prosthesis through the delivery opening and into the surgical cavity/pocket. In some embodiments, the bag can be scored along the vertical and horizontal lines as opposed to being cut such that the surgical professional can rip the bag along the vertical and horizontal lines to form the two opposed flaps at time of use. Generally, the polymeric material can have an interior surface selected as having high lubricity or can be formed of a hydrophilic material that becomes highly lubricated when exposed to saline.

In another representative embodiment, a prosthesis insertion device can comprise a bag defining having a pair of closed ends and a side oriented aperture. In proximity to the side oriented aperture, the surgical pocket can comprise a side aperture and a cover flap, wherein the bag can include a cover flap that extends over the side aperture to effectively close off the side aperture. A prosthesis can be inserted through the side aperture and suitable lubrication/wetting agents can be introduced into the bag through the side aperture. The cover flap can be closed over the side aperture and a delivery end can be opened by tearing or otherwise cutting the delivery end to a desired insertion size based on the size/volume of the prosthesis. The delivery end can be fabricated so as to define a rigid guide or tab that is positionable through a surgical incision. With the cover flap maintained over the side aperture, the surgical professional can physically manipulate the bag, by squeezing or rolling the bag, to deliver the prosthesis from the bag, through the delivery end and into a surgical cavity.

In another representative embodiment, a prosthesis insertion device can comprise a sheet or strip of polymeric material that includes a shaped-memory feature. Generally, the sheet or strip material can comprise a self-coiling design such that absent manipulation by a surgical professional, the sheet or strip material assumes a telescoping funnel or tube. Generally, the surgical professional can bias the sheet or strip of material into an open/flat arrangement with an internal surface facing upward. The surgical professional can then place or otherwise position the prosthesis bladder onto the sheet or strip. In some embodiments, the internal surface can be formed of a material having high lubricity or can be coated with a hydrophilic coating that has high lubricity when exposed to saline. When the surgical professional releases the sheet/strip of material, the material will snap back to its telescoping orientation with the bladder prosthesis now contained inside the telescoping orientation. At this point or prior to releasing the material, the surgical professional can apply saline to reduced friction between the bladder prosthesis and the internal surface. The surgical professional can then orient a delivery opening relative to a surgical incision and squeeze the telescoping orientation to force the bladder prosthesis out the delivery opening and into the surgical cavity/pocket. In some embodiments, the sheet or strip of material can comprise a rigid or malleable tab proximate the delivery opening to assist in positioning and retaining the delivery opening relative to the surgical incision.

In still another embodiment, a prosthesis insertion device can comprise a syringe-style delivery system for delivering a bladder prosthesis. Generally, the syringe can comprise a cylindrical body that terminates in a conical or funnel-like delivery end that defines a delivery opening. The cylindrical body can include an internal thread that cooperatively engages a corresponding plunger thread on a plunger. The bladder prosthesis can be placed into the cylindrical body. The cylindrical body can have a hydrophilic coating on an interior of the cylindrical body such that saline can be introduced into the cylindrical body to provide additional lubricity. The plunger can be engaged with the cylindrical body such that rotation of the plunger causes a plunger engagement surface to translate toward the delivery opening as the syringe and plunger threads rotatably engage. When the plunger engagement surface comes into contact with the bladder prosthesis, further rotation of the plunger causes the plunger engagement surface to bias the bladder prosthesis into the conical delivery end and ultimately out the delivery opening. The rotational engagement of the plunger thread and the syringe thread allow the user to provide a slow and deliberate pushing force to the bladder prosthesis which helps to prevent any binding that could damage the bladder prosthesis. The delivery opening can be positioned through a surgical incision such that as the bladder prosthesis is advanced out of the conical delivery end, the bladder prosthesis is directly inserted into the surgical cavity/pocket.

The various embodiments of prosthesis insertion and delivery devices disclosed herein provide for easier and quicker intraoperative delivery of silicone gel implants compared to other methods. In certain disclosed embodiments, no cutting or trimming of the delivery system is necessary thus saving time over other inventions and making them superior and distinct from conventional delivery devices. The prosthesis and insertion devices disclosed herein also protect the silicone breast implant from contamination of skin or other sources during the procedure. Use of the disclosed insertion and delivery devices can reduce the potential for biofilm on the implant and with less contamination, provide a reduction in the incidences of the most common breast augmentation complication, capsular contracture.

The above summary is not intended to describe each illustrated embodiment or every implementation of the subject matter hereof. The figures and the detailed description that follow along with the attached Appendix A more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1A:
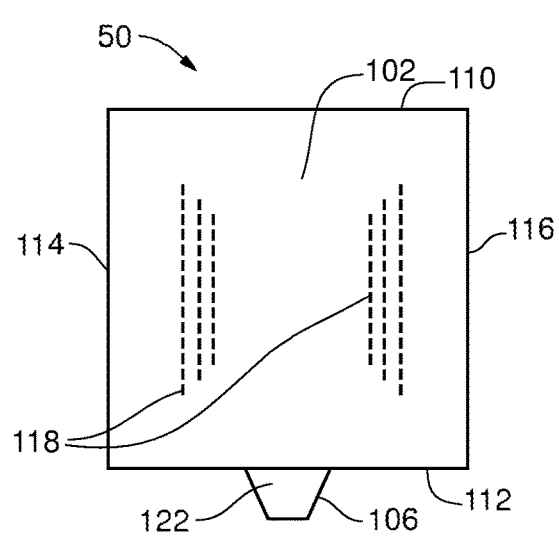
FIG. 1A is a schematic illustration of the top side of a sheet according to a representative embodiment of the present disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The following detailed description should be read with reference to the drawings m which similar elements in different drawings are numbered the same. The drawings, which are not necessarily to scale, depict illustrative embodiments and are not intended to limit the scope of the invention.

Referring generally to FIGS. 1-5 of the present disclosure, an apparatus for delivering a filled prostheses bladder into a surgical cavity generally comprises a delivery sheet 50, which includes a first or implant receiving surface 102, a second or manipulation assisting surface 104, and an insertion tab 106. Delivery sheet 50 can be fabricated from a transparent or semi-transparent plastic, or other suitable polymer materials which have sufficient properties including flexibility and non-elasticity. In addition, delivery sheet 50 can be provided as a sterile component; therefore, the fabrication material must be capable of withstanding at least one of several conventional sterilization techniques such as steam autoclave, chemical gas sterilization, or irradiation.

Figure 1B:
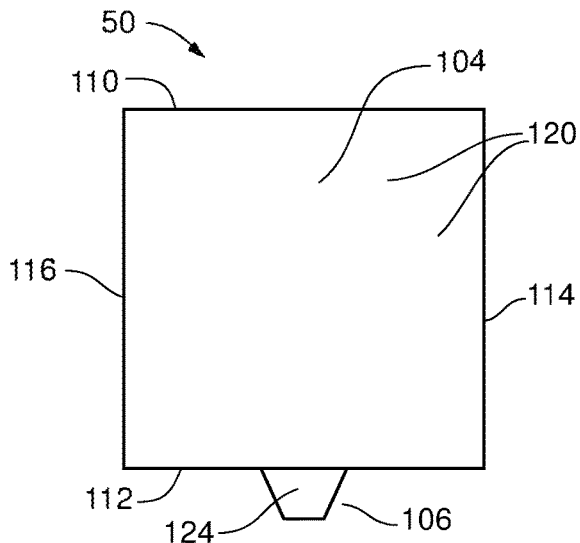
FIG. 1B is a schematic illustration of the bottom side of the sheet of FIG. 1A.

As best depicted in FIGS. 1A and 1B, delivery sheet 50 generally includes first surface 102, opposing second surface 104, and insertion tab 106. In one embodiment of the present disclosure, delivery sheet 50 is generally square in shape. The perimeter of delivery sheet 50 is formed by a top edge 110, a bottom edge 112, a first lateral edge 114, and a second lateral edge 116. Insertion tab 106 is centered along the horizontal axis of sheet 50, and coupled to bottom edge 112.

It is also envisioned that in alternative embodiments, top edge 110 and bottom edge 112 can be of different lengths. Similarly, top edge 110 and bottom edge 112 can be of equal lengths, but different lengths than lateral edges 114 and 116. Further, insertion tab 106 can be offset from the center of bottom edge 112.

As best depicted in FIG. 1A, first surface 102 includes a plurality of position indicia 118. In one embodiment of the present disclosure, plurality of positioning indicia 118 are centered vertically along the horizontal axis of sheet 50, are parallel to lateral edges 114 and 116, and are combined in pairs that increase in size proportionate to lateral distance from the center vertical axis of sheet 50. More particularly, plurality of positioning indicia 118 can vary in size, and position from the center axis of sheet 50, proportionate to increasing size of corresponding implants. First surface 102 can be fabricated from plastic, or other suitable polymer materials, that provide a low coefficient of friction. Further, the low coefficient of friction of first surface 102 can be supplemented by additional lubricants, including dry or powered lubricant products. Such products can be activated by being moistened, either by first surface 102 or another source, and offer an alternative to existing manual lubrication methods.

As best depicted in FIG. 1B, second surface 104 includes a plurality of manipulation assisting divots 120. In embodiments of the present disclosure, second surface 104 is a different color than first surface 102. Second surface 104 can be fabricated from similar plastic, or other suitable polymer materials, as first surface 102. Manipulation assisting divots 120 cover the entirety of second surface 104, and can be fabricated from similar plastic, or other suitable polymer materials, as surfaces 102 and 104. Alternatively, divots 120 can be fabricated from a more rigid plastic or polymer material than surfaces 102 and 104.

It is also envisioned that in alternative embodiments, second surface 104 can be the same color as first surface 102. Similarly, manipulation assisting divots 120 can be a different color than first surface 102 and/or second surface 104. Further, it is envisioned that a plurality of manipulation assisting divots 120 can be positioned in bands on the lateral portions of second surface 104.

Figure 5A:
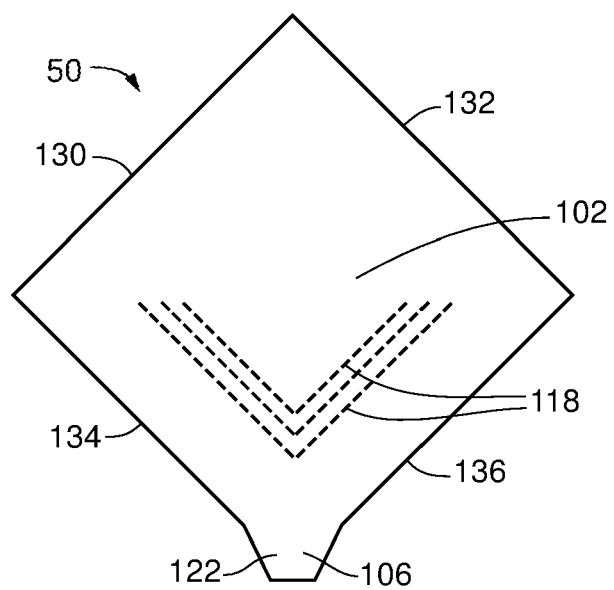
FIG. 5A is a schematic illustration of the top side of a sheet according to another representative embodiment of the present disclosure.

As best depicted in FIGS. 1A, 1B and 5A insertion tab 106 includes an insertion assisting surface 122 and an insertion supporting surface 124. In embodiments of the present disclosure, insertion assisting surface 122 is fabricated from the same plastic or polymer material as first surface 102, and insertion supporting surface 124 is fabricated from the same plastic or polymer material as second surface 104. Similar to second surface 104, the entirety of insertion supporting surface 124 is covered by manipulation assisting divots 120. Moreover, in embodiments of the present disclosure, insertion tab 106 is generally trapezoidal in shape, and is positioned along the bottom of delivery sheet 50.

It is also envisioned that in alternative embodiments, insertion tab 106 can be fabricated from a more rigid plastic or polymer than surfaces 102 and 104. It is also envisioned that insertion tab 106 can be generally square or rectangular in shape. Further, insertion tab 106 can include a concave curvature structure.

Figure 2:
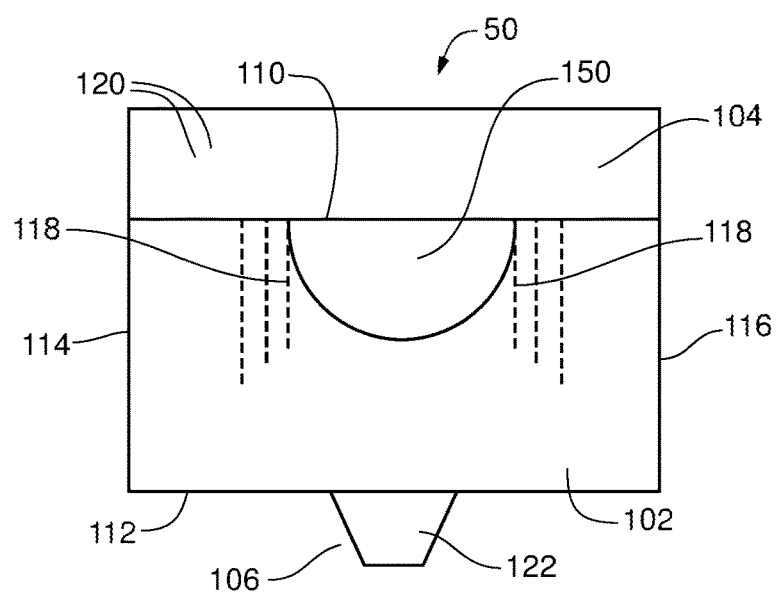
FIG. 2 is a schematic illustration of a system for delivering a filled prostheses bladder into a surgical cavity, according to a representative embodiment of the present disclosure.
Figure 3A:
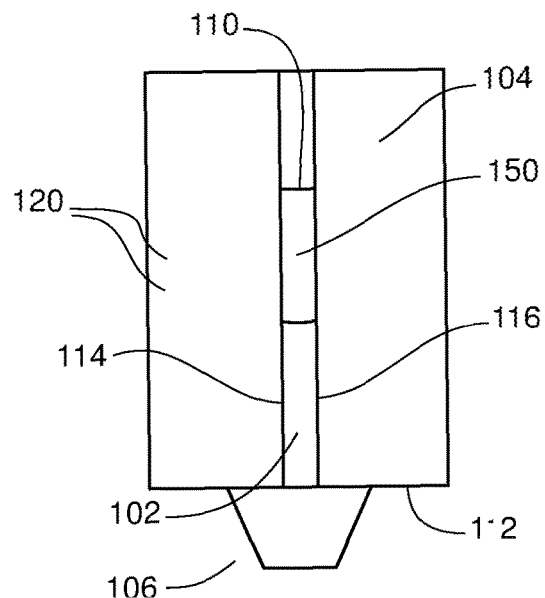
FIG. 3A is a schematic illustration of the system for delivering a filled prostheses bladder of FIG. 2, according to a representative embodiment of the present disclosure.
Figure 3B:
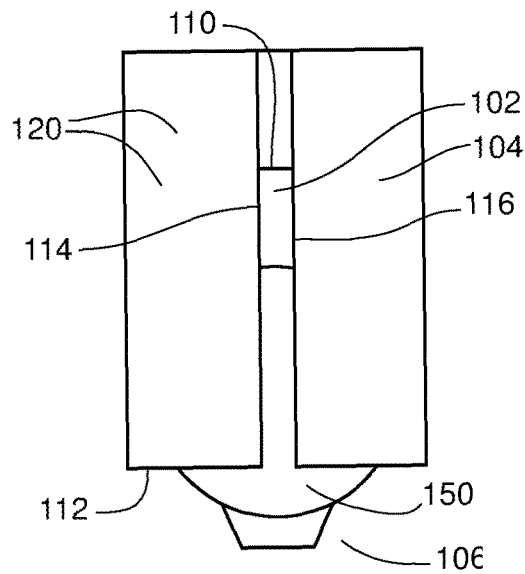
FIG. 3B is a schematic illustration of the system of FIG. 3A, after manual manipulation.

In operation, as best illustrated in FIGS. 2, 3A and 3B delivery sheet 50 receives filled prostheses bladder or implant 150 on first surface 102. Implant 150 can be precisely positioned, based on size, using positioning indicia 118. Once in place, top edge 110 can be folded over implant 150, surrounding implant 150 with low friction first surface 102 and exposing manipulation assisting divots 120 of second surface 104 to the user. First lateral edge 114 and second lateral edge 116 can then be folded over implant 150 toward the center of delivery sheet 50. Depending on the size of implant 150, implant 150 can be covered on the top and bottom by first surface 102 and manipulation assisting divots 120 can be exposed across the top of implant 150. Once the user is satisfied with the covering and positioning of implant 150, the user can move sheet 50 and implant 150 to the perimeter of the surgical site.

When in position, insertion tab 106 can be placed on the edge of the surgical cavity. The user can apply manual pressure to sheet 50 and implant 150 to move implant 150 down sheet 50, toward insertion tab 106 and the surgical cavity. The minimal frictional forces of first surface 102, and the manipulation assisting divots 120 of second surface 104, permit the user to precisely control movement of implant 150. As the user manipulates implant 150 down sheet 50 toward the surgical cavity, insertion tab 106 acts to guide the user and facilitate shoehorning implant 150 into the surgical cavity.

Figure 4A:
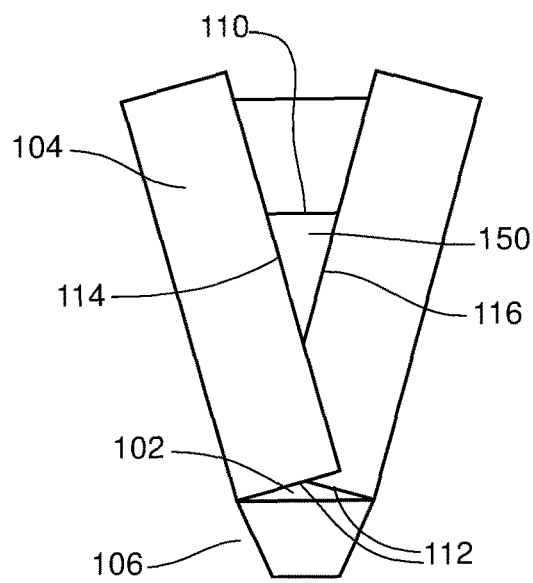
FIG. 4A is a schematic illustration of the system for delivering a filled prostheses bladder of FIG. 2, according to another representative embodiment of the present disclosure.
Figure 4B:
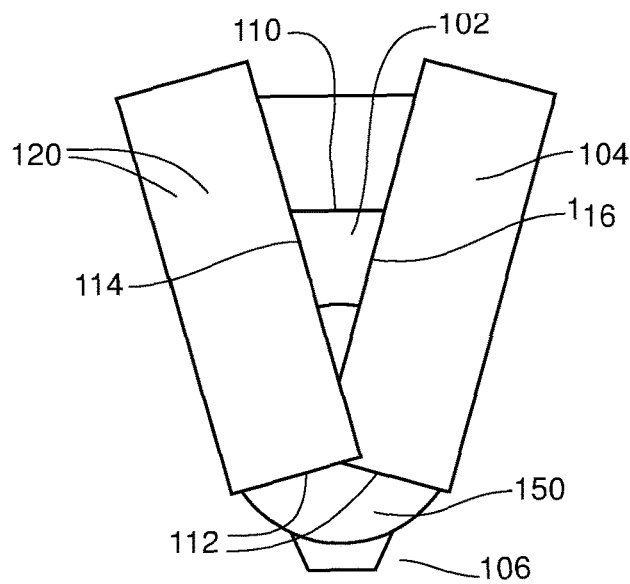
FIG. 4B is a schematic illustration of the system of FIG. 4A, after manual manipulation.

In another embodiment of the present disclosure, as illustrated in FIGS. 4A and 4B, once implant 150 is in place, top edge 110 can be folded over implant 150. First lateral edge 114 and second lateral edge 116 can be folded at angles to encapsulate implant 150 in a generally triangular shaped covering. Once the user is satisfied with the covering and positioning of implant 150, the user can move sheet 50 and implant 150 to the perimeter of the surgical site, and manipulate implant 150 into the surgical cavity.

It is also envisioned that in an alternative embodiment, once implant 150 is in place, and top edge 110 is folded over implant 150, lateral edges 114 and 116 can be rolled to encapsulate implant 150 in a generally conical shaped covering. Once the user is satisfied with the covering and positioning of implant 150, the user can move sheet 50 and implant 150 to the perimeter of the surgical site, and manipulate implant 150 into the surgical cavity.

As best depicted in FIG. 5A, in another embodiment of the present disclosure, delivery sheet 50 generally comprises first surface 102, opposing second surface 104 and insertion tab 106, and is generally rhombus in shape. The perimeter of delivery sheet 50 is formed by a first top edge 130, a second top edge 132, a first bottom edge 134, and a second bottom edge 136. First top edge 130 and second top edge 132 are of equal lengths, and first bottom edge 134 and second bottom edge 136 are of equal lengths. In embodiments, first surface 102 of sheet 50 includes plurality of positioning indicia 118. Positioning indicia 118 are combined in pairs, arranged perpendicular to one another near bottom edges 134 and 136, and increase in size proportionate to distance from the center of sheet 50. More particularly, plurality of positioning indicia 118 can vary in size, and position from the center of sheet 50, proportionate to increasing size of corresponding implants. Insertion tab 106 is centered at the bottom of delivery sheet 50, coupling to sheet 50 at the conjunction between first bottom edge 134 and second bottom edge 136. Insertion tab 106 can have an insertion assisting surface 122.

Figure 5B:
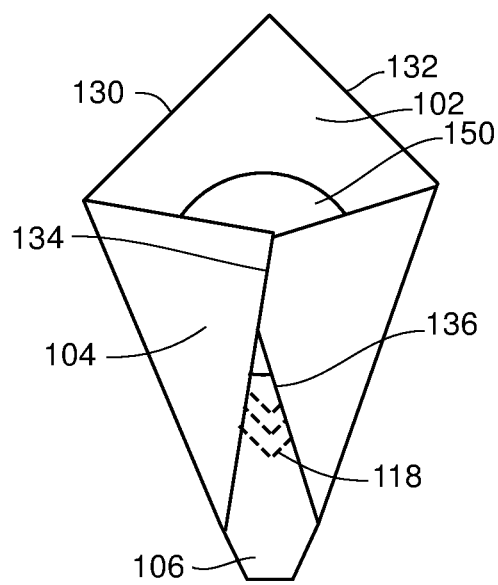
FIG. 5B is a schematic illustration of a system for delivering a filled prostheses bladder into a surgical cavity, according to a representative embodiment of the present disclosure.
Figure 5C:
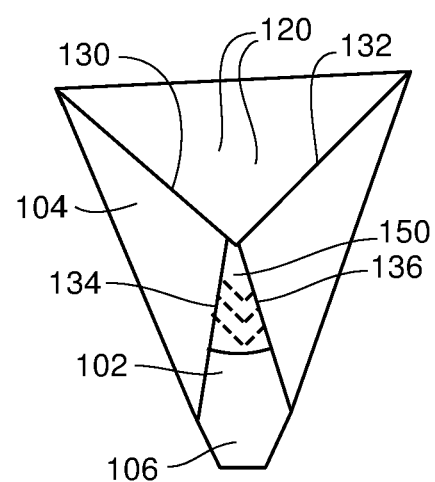
FIG. 5C is a schematic illustration of the system of FIG. 5B, after manual manipulation.
Figure 7:
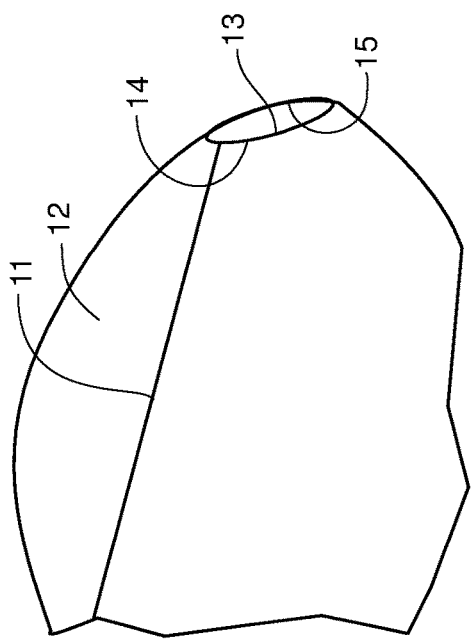
FIG. 7 is a perspective view of an insertion end of the prosthesis insertion device of FIG.
Figure 9:
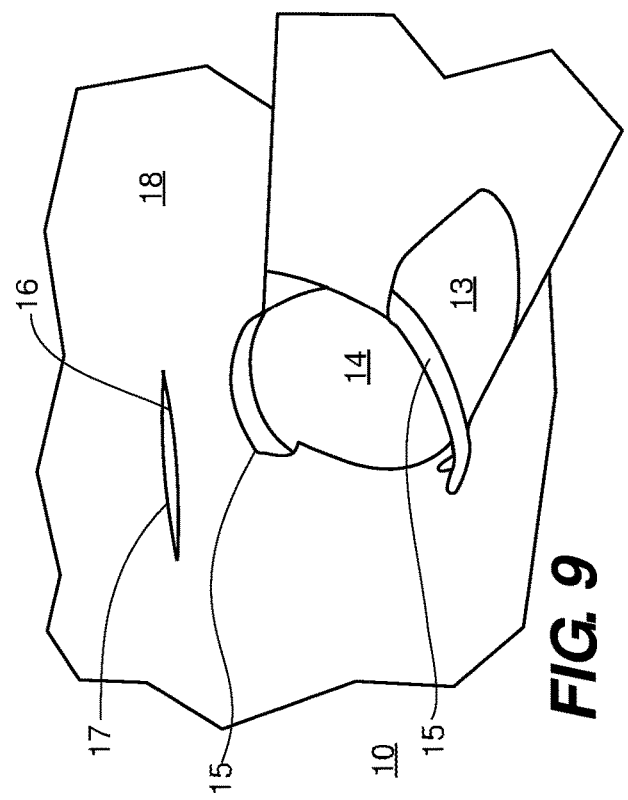
FIG. 9 is a perspective, end view of the prosthesis insertion device of FIG. 6.
Figure 6:
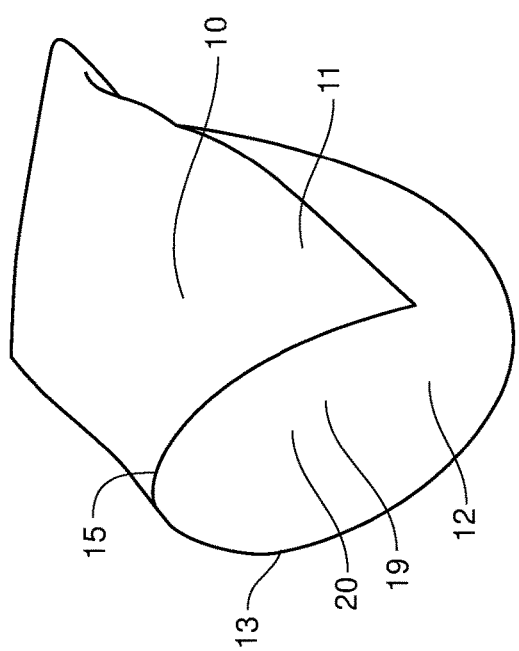
FIG. 6 is a perspective view of a prosthesis insertion device according to another representative embodiment of the present invention.
Figure 8:
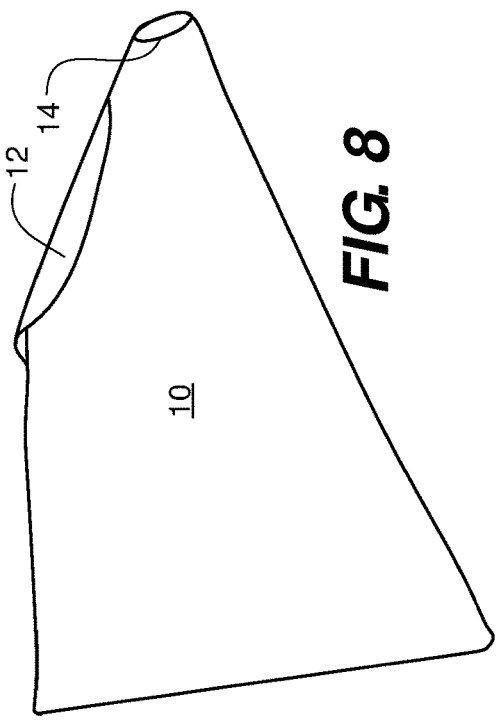
FIG. 8 is a top view of the prosthesis insertion device of FIG. 6.

In operation, as best illustrated in FIGS. 5A and 5B delivery sheet 50 receives filled prostheses bladder or implant 150 on first surface 102. Implant 150 can be positioned, based on size, using positioning indicia 118. Once in place, first bottom edge 134 and second bottom edge 136 can be individually folded upward toward the center of sheet 50, over implant 150, covering implant 150 with low friction first surface 102 and exposing manipulation assisting divots 120 of second surface 104. Then, first top edge 130 and second top edge 132 can be folded together toward the center of sheet 50, over implant 150, to encapsulate implant 150 in a generally triangular shaped covering. Depending on the size of implant 150, implant 150 can be covered on the top and bottom by first surface 102, and manipulation assisting divots 120 can be exposed across the top of implant 150. Once the user is satisfied with the covering and positioning of implant 150, the user can move sheet 50 and implant 150 to the perimeter of the surgical site, and manipulate implant 150 into the surgical cavity.

It is also envisioned that in an alternative embodiment, once implant 150 is in place, first bottom edge 134 and second bottom edge 136 can be rolled over implant 150 to encapsulate implant 150 in a generally conical shaped covering. Once the user is satisfied with the covering and positioning of implant 150, the user can move sheet 50 and implant 150 to the perimeter of the surgical site, and manipulate implant 150 into the surgical cavity.

In another embodiment as shown in FIGS. 6-11, a representative embodiment of a prosthesis insertion device 6 can comprise an applicator body 10 having a closed end 8. Applicator 10 can be formed of any medical and application appropriate polymeric material such as for example, a sheet of Mylar. In addition, the material can be selected as having advantageous properties, for example, hydrophilic properties or can be coated to impart properties or for subsequent delivery of lubrication or sterilization agents. The applicator 10 can comprise an internal first flap 11, an external second flap 12. A distal orifice 14 generally defines a delivery end and can comprise a one or more insertion guides 13. Each insertion guide 13 can include an insertion guide retention lip 15. Generally, manipulation of the internal first flap 11 relative to the external second flap 12 along with the close end 8 can define a device pocket 20. In some embodiments, the externally visible surface of the internal first flap can include an overlap guide or marking based on prosthesis size/volume so as to properly orient the external second flap 12 to have a desired opening size for the distal orifice 14. In some embodiments, the abutting surfaces of the internal first flap 11 and external second flap 12 can include surface treatments to increase friction, textures including for example, complimentary ribs or bumps that at least partially engage or even adhesives such that a surgical professional is assisted in maintaining the appropriate overlap of the external second flap 12 relative to the internal first flap 11 and thus maintain the appropriate opening size for the distal orifice 14.

Figure 11:
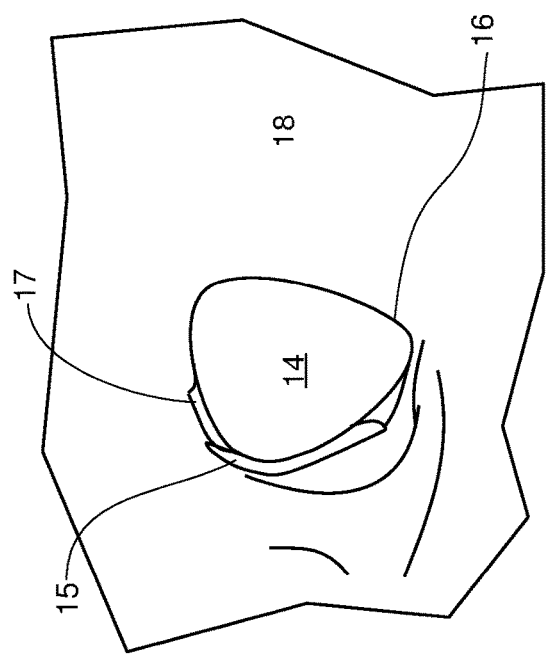
FIG. 11 is an end view of the prosthesis insertion device of FIG. 10 taken from within the incision.
Figure 13:
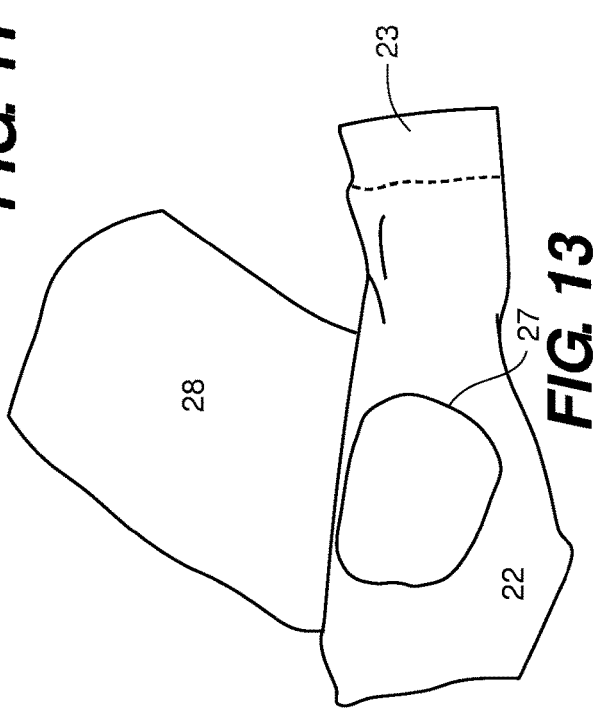
FIG. 13 is a top view of the prosthesis insertion device of FIG. 12.
Figure 10:
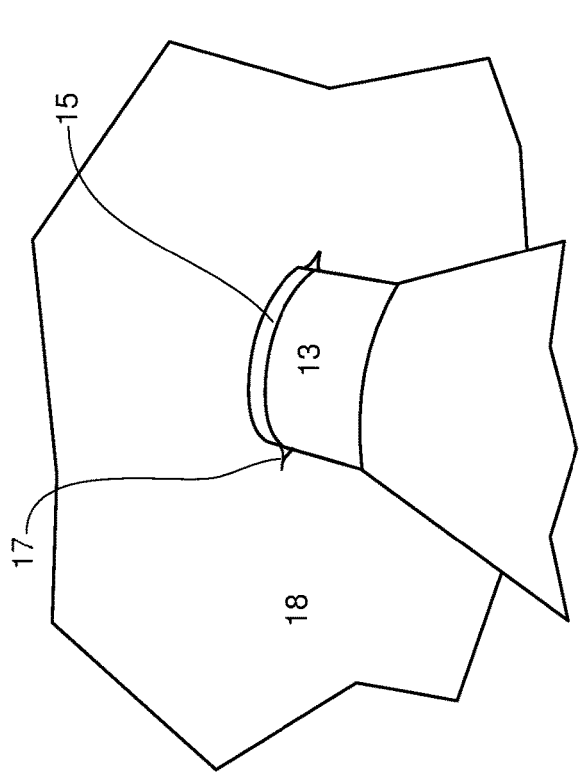
FIG. 10 is as perspective, end view of the prosthesis insertion device of FIG. 9 accessing an incision.
Figure 12:
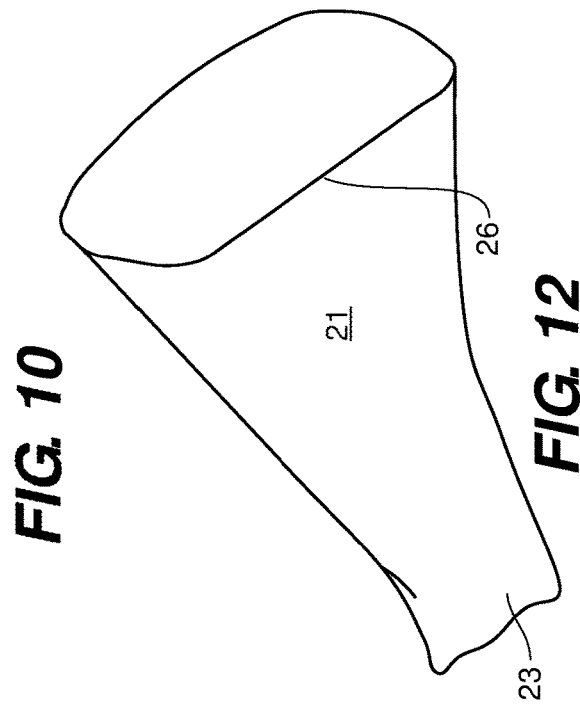
FIG. 12 is a perspective view of a prosthesis insertion device according to another representative embodiment of the present invention.

As shown in FIGS. 10 and 11, the insertion guides 13 allow the surgical professional to orient the distal orifice 14 relative to an incision 1 7 in skin tissue 18. The insertion guides 13 can be directed through the incision 17 and into a surgical cavity 20, whereby the insertion guide retention lip 15 is positioned within the surgical cavity 20 and retains the distal orifice 14 in communication with the incision 17. The surgical professional can then manipulate the applicator body 10 for example, by rolling or squeezing at the closed end 8 to deliver the prosthesis through the distal orifice 14 and into the surgical cavity 20.

Figure 15:
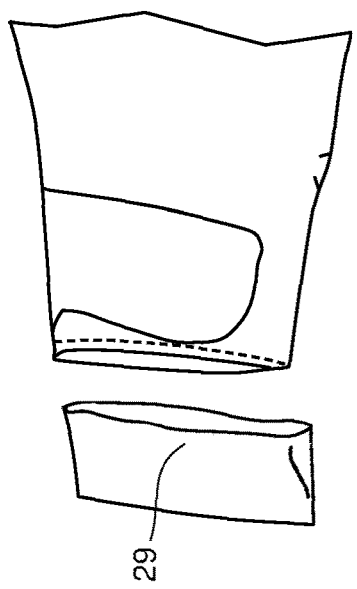
FIG. 15 is a top view of the prosthesis insertion device of FIG. 12 with a distal end removed to size an insertion opening.
Figure 17:
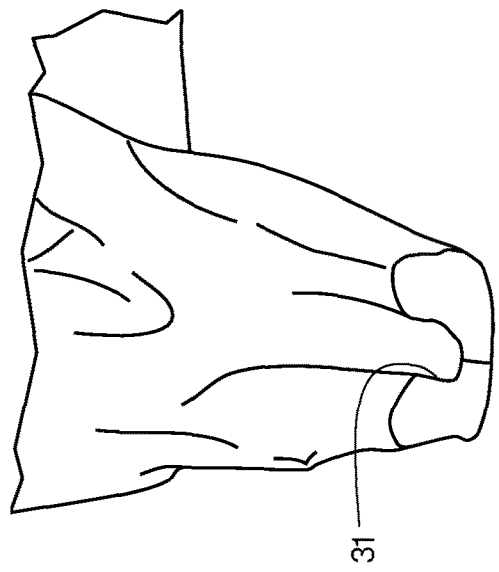
FIG. 17 is a perspective, end view of the prosthesis insertion device of FIG. 11.
Figure 14:
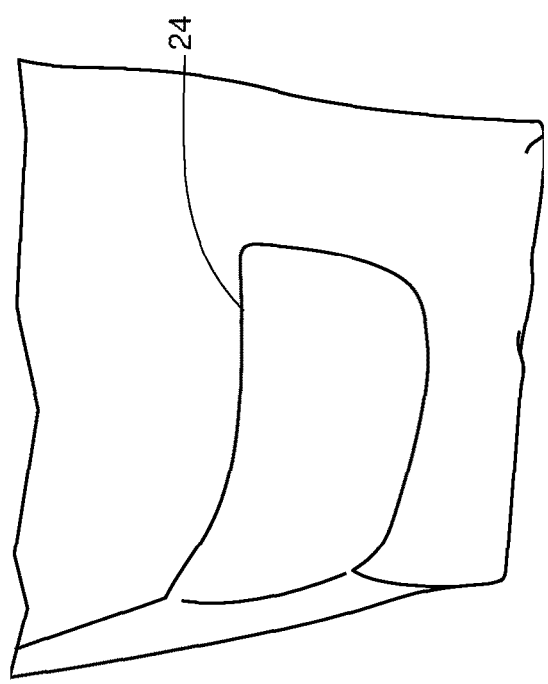
FIG. 14 is a top view of the prosthesis insertion device of FIG. 12.
Figure 16:
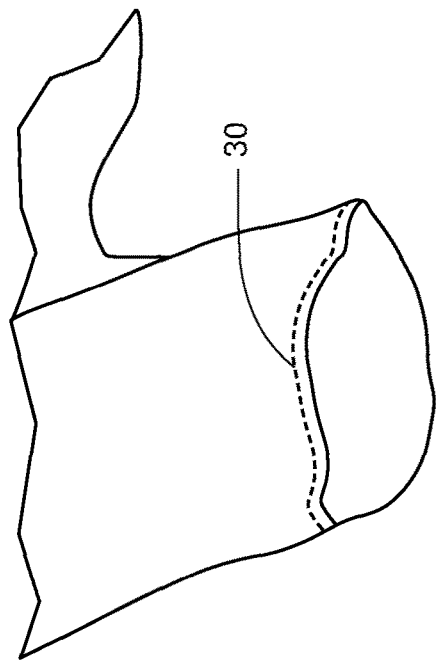
FIG. 16 is a perspective, end view of the prosthesis insertion device of FIG. 11.
Figure 19:
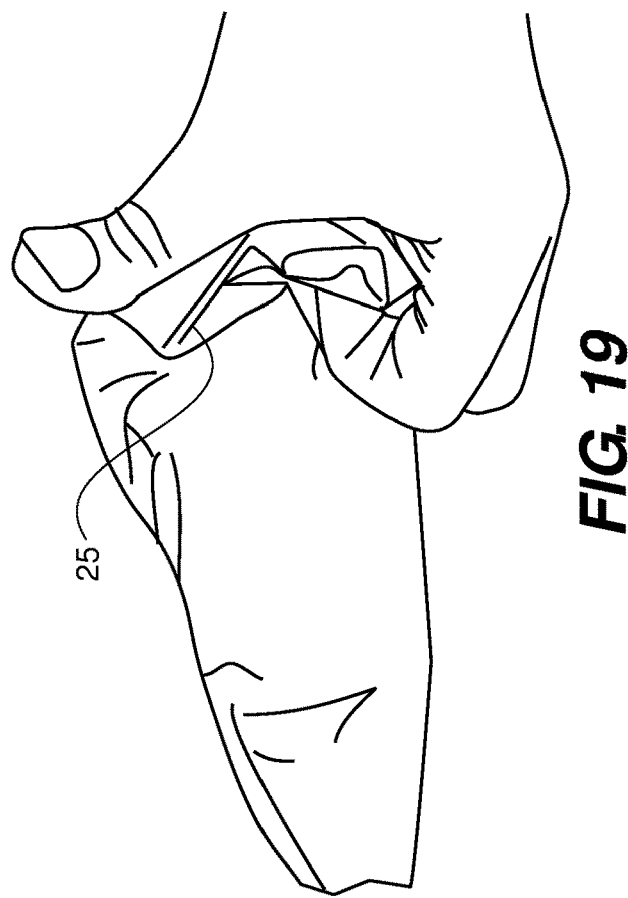
FIG. 19 is a top view of the prosthesis insertion device of FIG. 11 with a closed end being manipulated to deliver the prosthesis.
Figure 18:
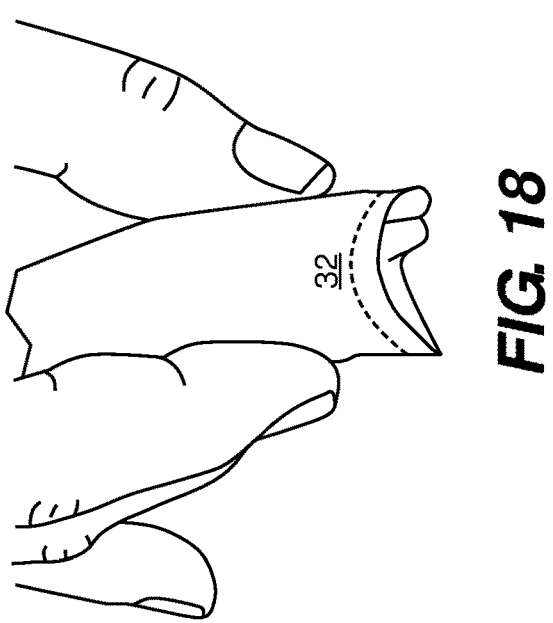
FIG. 18 is a perspective, end view of the prosthesis insertion device of FIG. 11.

In another embodiment as shown in FIGS. 12-19, a prosthesis insertion device 21 can comprise a cylindrical or conical body 21 having a sealed distal end 23 and a sealed proximal end 25. The prosthesis insertion device 21 can include a compressible insertion guide 24 located near the sealed distal end 23. The conical body 21 can include a lateral or side aperture 27 with a corresponding lateral or side flap 28. Generally, a prosthesis can be inserted through the side aperture 27 and a suitable lubrication or wetting agent can be added into the conical body through the side aperture 27. The side flap 28 can be positioned over the side aperture 27 to effectively close the prosthesis insertion device 21. As shown in FIG. 15, the user can cut or otherwise tear the sealed distal end 23 to expose a distal orifice 29. Generally, the sealed distal end 23 can include markings based on the size/volume of the prosthesis such that the distal orifice 29 is cut or torn to a desired size. Using the compressible insertion guide 24, the user can compress and/or shape the distal orifice 29 for introduction through the incision 17 and into the surgical cavity 20 similar to that shown in FIGS. 10 and 11.

Figure 20:
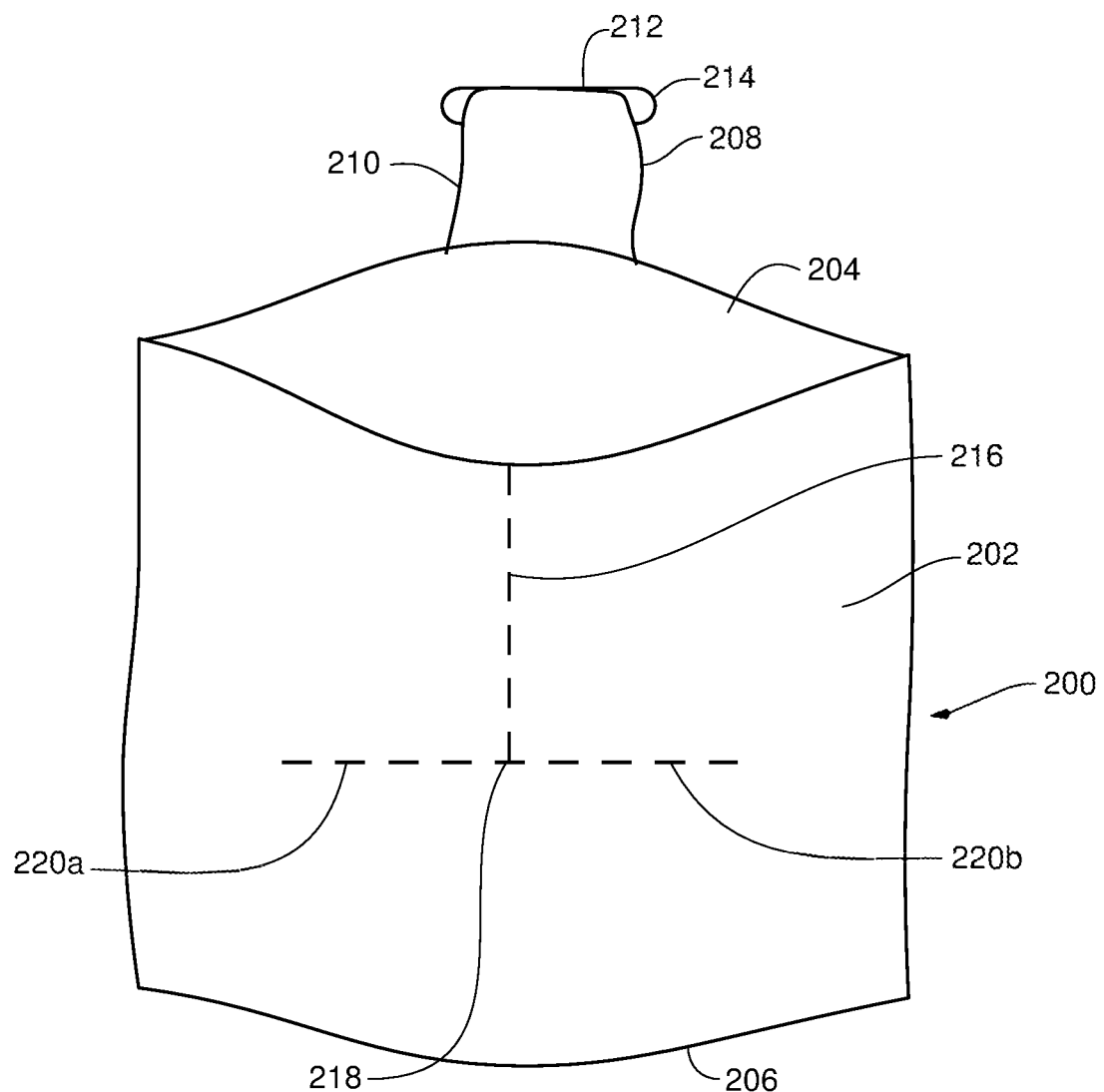
FIG. 20 is a top view of an implant prosthesis insertion device according to another representative embodiment of the present invention.
Figure 21:
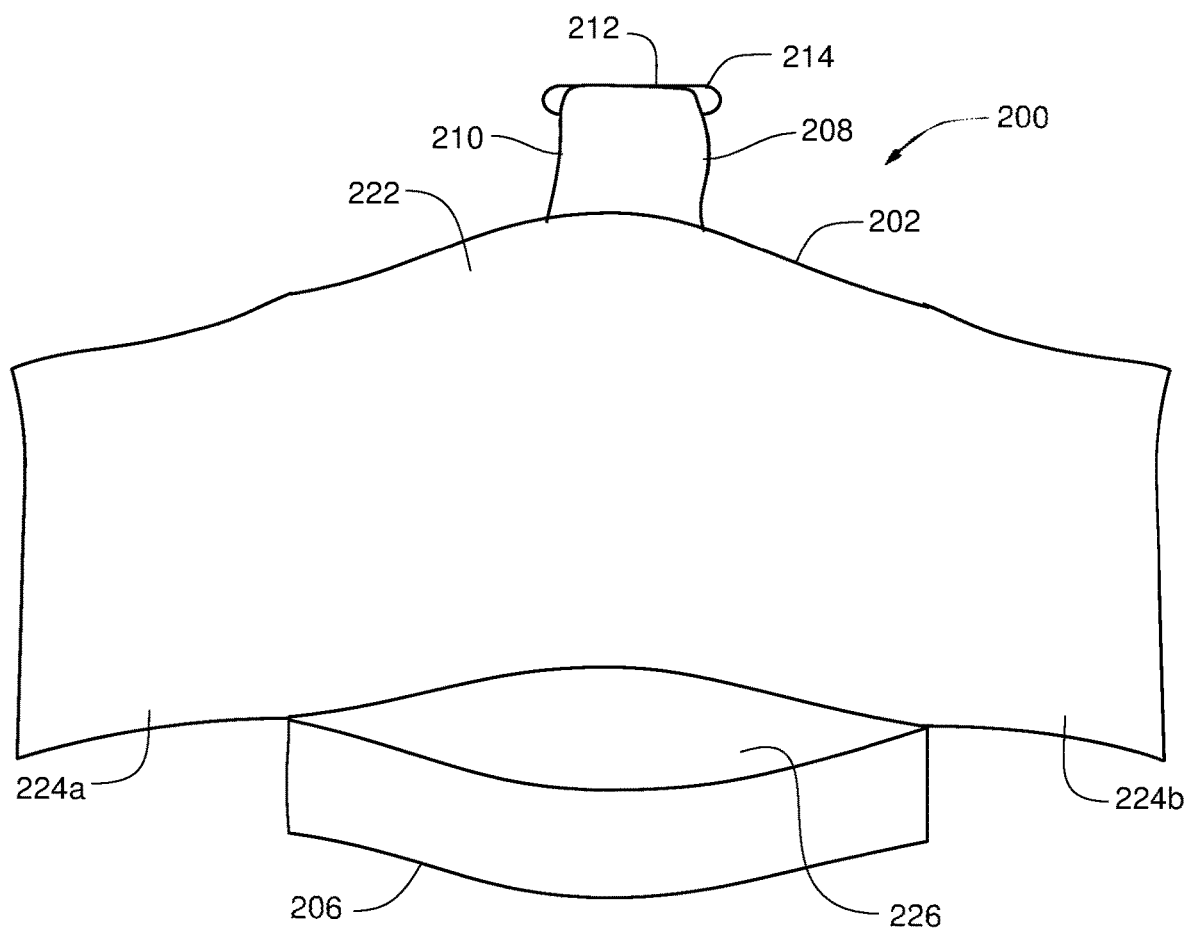
FIG. 21 is a top view of the implant prosthesis insertion device of FIG. 20 including a pair of overlappable flaps.
Figure 22:
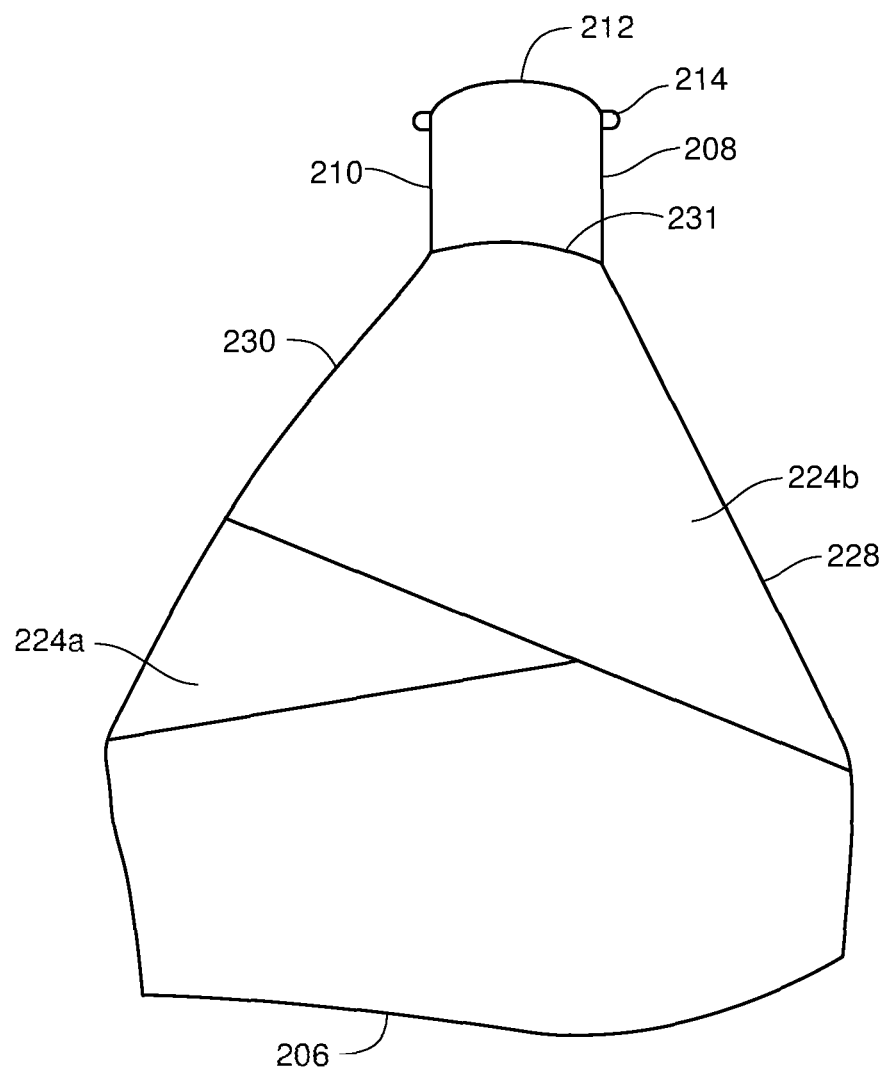
FIG. 22 is a top view of the implant prosthesis insertion device of FIG. 20 with the overlappable flaps formed into a conical shape.
Figure 23:
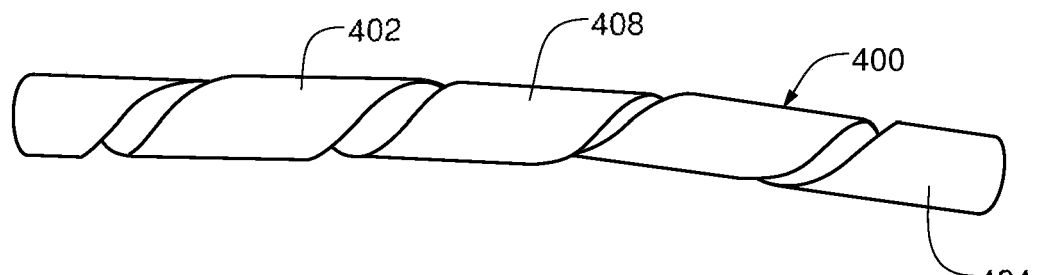
FIG. 23 is a top view of an embodiment of an implant prosthesis insertion device formed of an elongated strip with shape memory properties.
Figure 24:
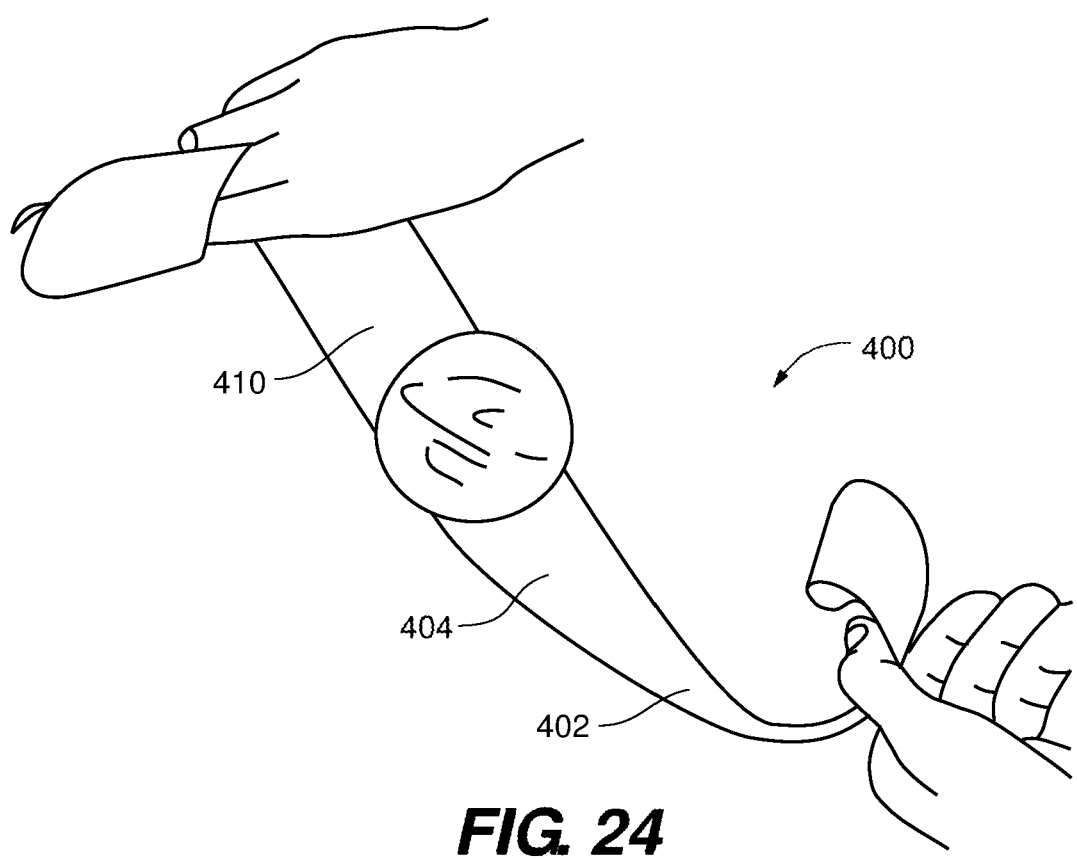
FIG. 24 is a top view of the implant prosthesis insertion device of FIG. 23 formed into a flat orientation for placement of an implant prosthesis.
Figure 25:
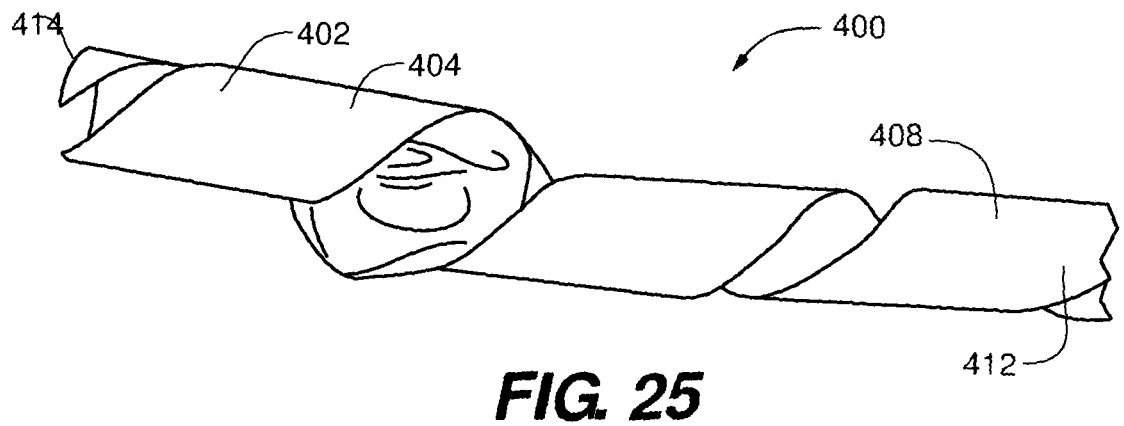
FIG. 25 is a top view of the implant prosthesis insertion device of FIG. 23 with the implant prosthesis retained within the implant prosthesis insertion device.
Figure 26:
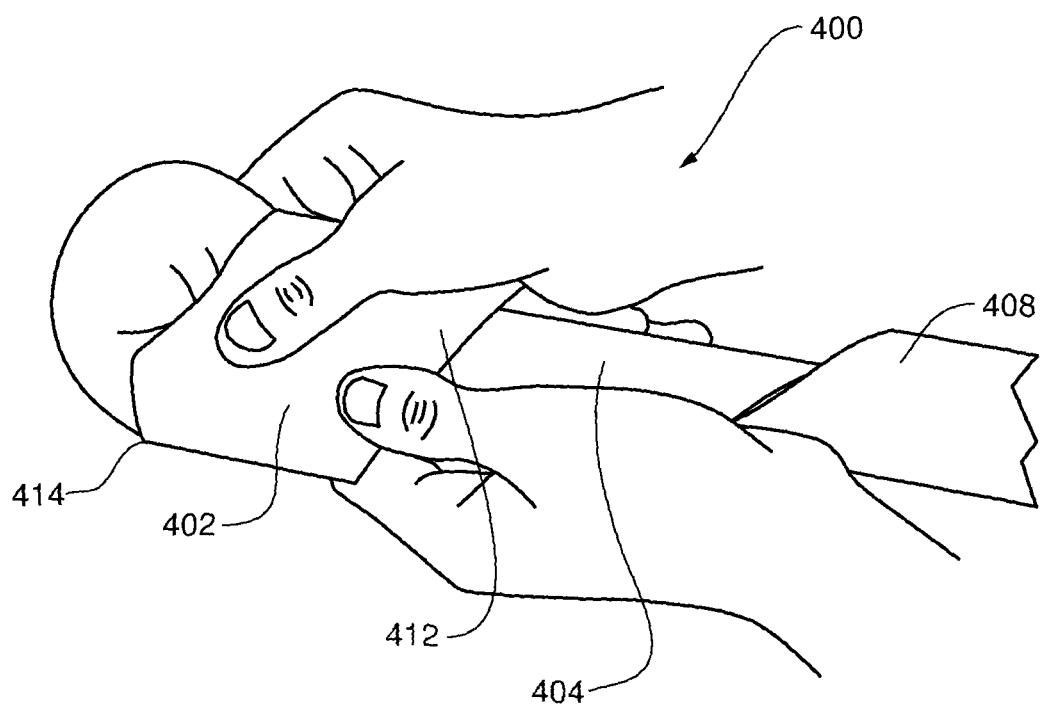
FIG. 26 is a top view of the implant prosthesis insertion device of FIG. 23 with the implant prosthesis being delivered from a delivery end of the implant prosthesis insertion device.

In another embodiment as shown in FIGS. 20-22, a prosthesis insertion device 200 can comprise a variation to prosthesis insertion device 6 in which fabrication begins with a structure 202 having an open end 204 and a closed end 206. As shown in FIG. 20, structure 202 can substantially resemble a conventional polymeric bag formed of the same polymeric materials as delivery sheet 50, prosthesis insertion device 6 and prosthesis insertion device 21. Generally, the structure 202 can include a malleable or rigid guide 208 at the open end 204. The malleable or rigid guide 208 can include a guide body 210 that terminates in a guide end 212. The guide end 212 can comprise a retention member 214, for example, a lip or one or more tabs extending laterally from the guide end 212.

In order to form the prosthesis insertion device 200, the structure 202 can be cut along a vertical line 216 that extends from the open end 204 toward the closed end 206 but does not reach the closed end 206 as sheen in FIG. 20. The structure 202 can then be cut from a vertical cut end point 218 on a horizontal line 220a and horizontal line 220b. Horizontal lines 220a, 220b are each cut only along a portion of the circumference of the structure 202 such the closed end 206 is not separated from an upper portion 222 of the structure 202. In an alternative embodiment, vertical line 216 and horizontal lines 220a, 220b can be scored as opposed to being cut, thus allowing a surgical profession to place an implant prosthesis into the open end of structure 202 and then tear the structure 202 along the scored lines of vertical line 216 and horizontal lines 220a, 220b to form the prosthesis insertion device 200 with the implant prosthesis already positioned in the closed end 206.

Regardless of whether the vertical line 216 and horizontal lines 220a, 220b are cut or torn along scores, a pair of insertion flaps 224a, 224b are defined as shown in FIG. 21. With the implant prosthesis positioned within a retaining pocket 226 defined at the closed end 206, a lubricating agent, such as saline, can be added to the retaining pocket 226. The surgical professional can then wrap and overlap the insertion flaps 224a, 224b such that the upper portion 222 is formed into a conical shape 228, such as a delivery funnel 230 having a delivery opening 231 as shown in FIG. 22. The surgical professional can then direct the malleable or rigid guide 208 into and through the surgical incision such that the guide end 212 resides within the surgical pocket in a manner similar to that shown in FIGS. 10 and 11. With the guide end 212 within the surgical pocket, the retention member 214 can help to retain the guide end 212 by interfacing with an interior wall of the surgical pocket. The surgical professional can then squeeze or roll the closed end 206 such that the implant prosthesis is directed through the delivery funnel 230, out the delivery opening 231 and into the surgical pocket.

Figure 27:
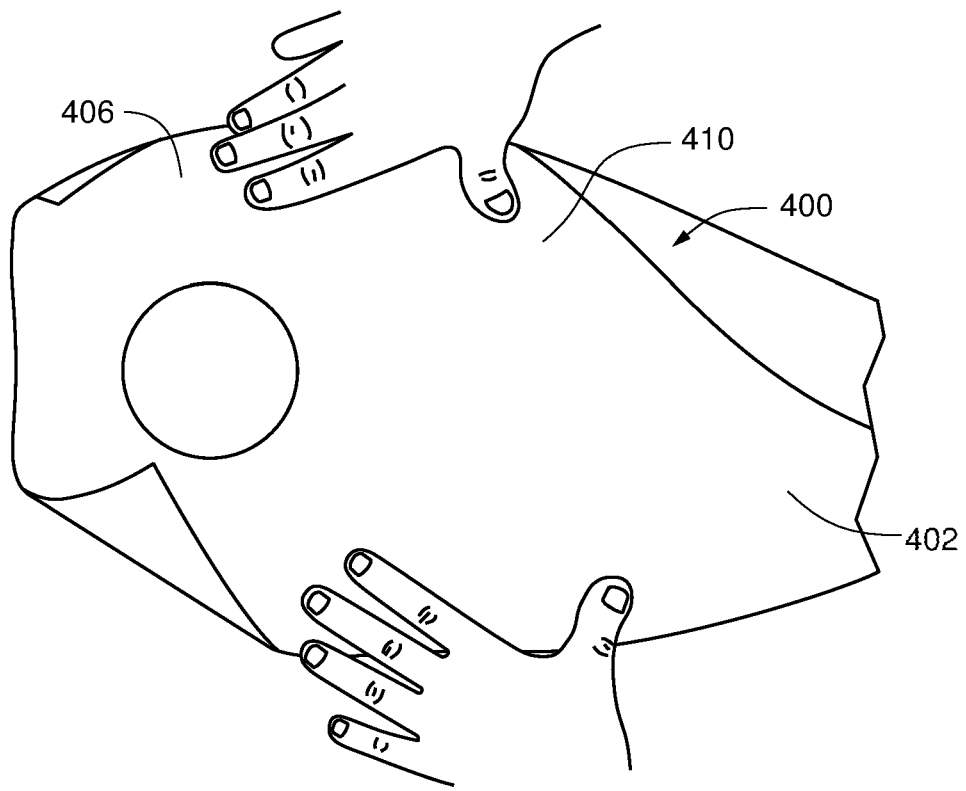
FIG. 27 is a top view of an embodiment of an implant prosthesis insertion device formed of a rectangular strip with shape memory properties formed into a flat orientation for placement of an implant prosthesis.
Figure 28:
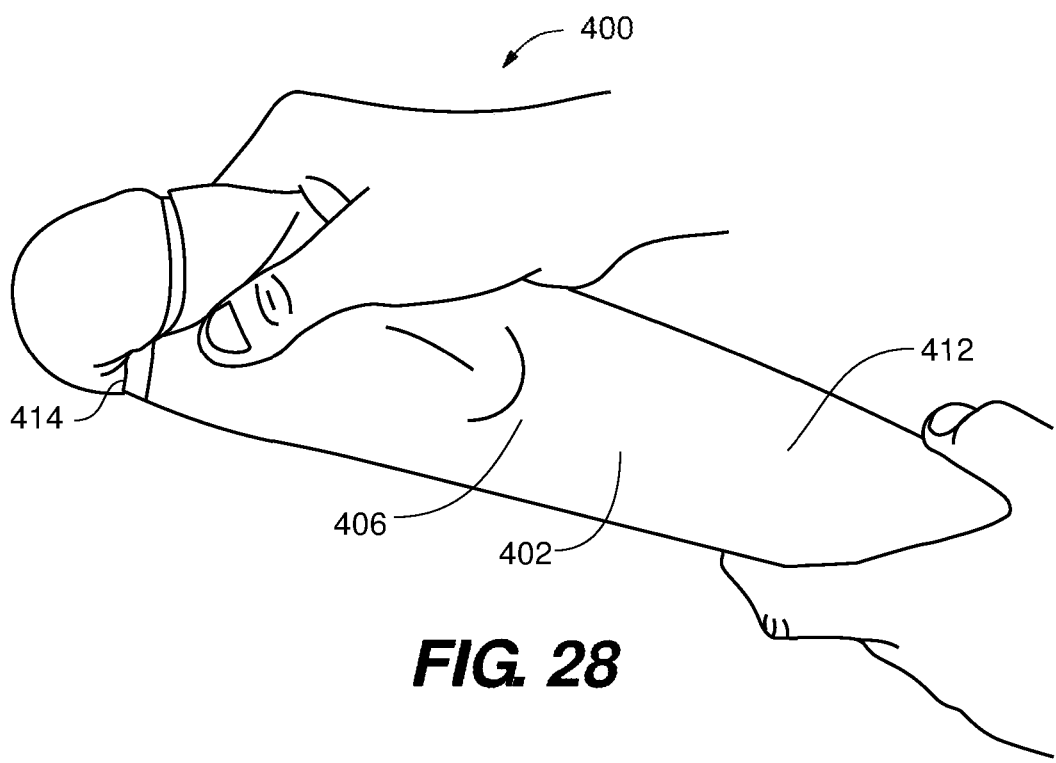
FIG. 28 is a top view of the implant prosthesis insertion device of FIG. 27 with the implant prosthesis being delivered from a delivery end of the implant prosthesis insertion device.

In yet another representative embodiment of an implant prosthesis delivery device 400 as shown in FIG. 23-28 can comprise a sheet 402, for example, an elongated strip 404 as shown in FIGS. 23-26 or a square or rectangular sheet 406 as shown in FIGS. 27 and 28. Regardless of the shape 402, the sheet 402 can be fabricated so as to possess shape memory properties such that the sheet desires to assume a conical or tubular shape 408, when not being biased to an open or flat orientation 410. Generally, a surgical professional can remove the implant prosthesis delivery device 400 from an implant kit and bias the implant prosthesis device 400 to the open or flat orientation 410. The surgical professional then places the implant prosthesis on the elongated strip 404 or square 406 and then releases the sheet 402. Once released, the sheet 402 immediately "snaps" back and assumes the conical or tubular shape 408 with the implant prosthesis now captured within an interior of the implant prosthesis delivery device 400. At this point, the surgical professional can add a suitable lubricant, for example, saline to the interior of the implant prosthesis device 400. The surgical professional can then close and being rolling or squeezing a distal end 412 of the implant prosthesis device 400 such that the implant prosthesis is biased toward a delivery end 414. Though not depicted, delivery end 414 can include a malleable or rigid guide and a retention member, for example, a lip or tabs as previously described with respect to other embodiments of the present invention. With delivery end 414 positioned through or proximate the surgical incision, the surgical profession delivers the implant prosthesis out the delivery end 414 and into the surgical pocket.

As discussed in the prior embodiments, various embodiments of implant prosthesis delivery devices have been disclosed that are generally formed from polymeric sheets. The materials of these polymeric sheets are generally selected as possessing suitable characteristics for use in surgical settings. Generally, these properties include compatibility with conventional sterilization techniques as well as resistance to tearing or ripping of the material, except for situations involving intentional scoring of the material. In some embodiments, the polymeric sheet can be selected as having different properties on an exterior versus interior surface. In some embodiments, the exterior and interior surface can have different colors such that the surgical professional can quickly identify the proper orientation of the polymeric sheet. In addition, it may be desirable that the exterior surface possessed enhanced gripping or tactile feel characteristics and easily accept visual indicia. At the same time, it may be desirable that the interior surface have increased lubricity, for example, by having a hydrophilic surface that has increased lubricity in the present of saline/water. In order to achieve the desired material properties, the polymeric sheet can comprise a single layer or two or more layers such that the desired properties for the exterior and interior surfaces are achieved. Alternatively, one or both of the exterior and interior surfaces can have a surface coating intended to impart the desired properties, for example, a hydrophilic coating on the interior surface such as, for example, Lubrilast™ available from AST Products, Inc. In one embodiment, the polymeric sheet can be formed of one or more layers of Mylar® (biaxially-oriented polyethylene terephthalate (PET)) selected for its high tensile strength and chemical and dimensional stability.

Figure 29:
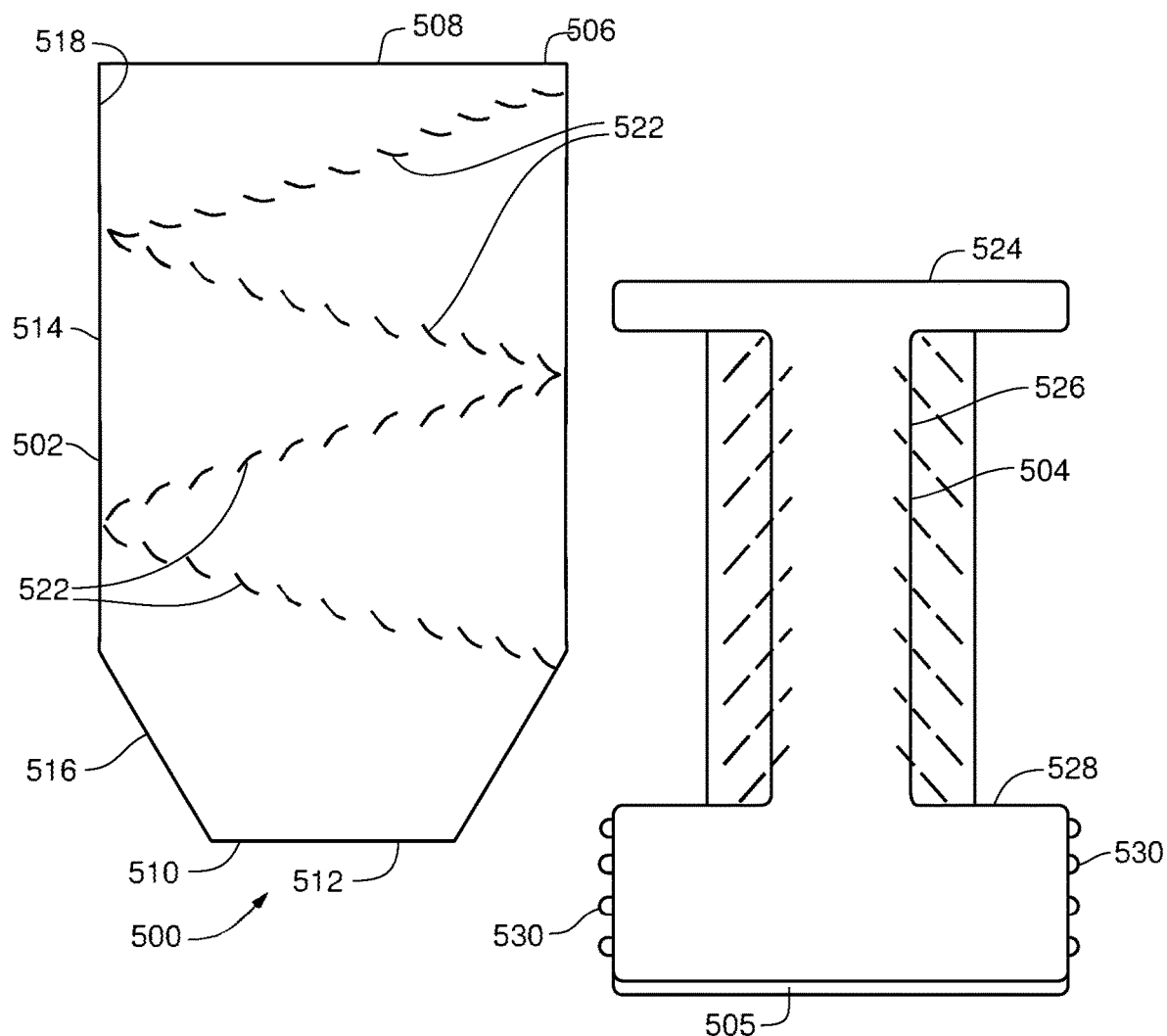
FIG. 29 is a side view of a syringe-style implant prosthesis insertion device according to a representative embodiment of the present invention.

In another embodiment, an implant prosthesis insertion device 500 can take the form of a syringe-style delivery device including a syringe body 502, a rotatable plunger 504 and a sealing member 505 as shown in FIG. 29. Generally, the syringe body 502 defines a receiving end 506 having a receiving aperture 508 and a delivery end 510 having a delivery aperture 512. The cylindrical body 502 further defines a receiving portion 514 and a delivery funnel 516. An inner wall 518 of the receiving portion 514 includes a body thread 522. Rotatable plunger 504 generally comprises a handle portion 524, a handle shaft 526 and an engagement portion 528. Engagement portion 528 is generally sized and shaped to fit within the receiving portion 514 and includes an external engagement thread 530 that is configured to threadably engage the body thread 522. Seal member 505 is generally sized and shaped to snugly fit within the receiving portion 520 and comprise a suitable sealing material such as, for example, silicone rubber and the like.

To use implant prosthesis insertion device 500, a user can place an implant prosthesis into the cylindrical body 502 through the receiving aperture 508. Next the user can place the seal member 505 on top of and in contact with the implant prosthesis through the receiving aperture 508. Finally, the user can orient the rotatable plunger 504 such that the engagement portion 528 is aligned with and enters the receiving aperture 508. By turning the handle portion 524, the surgical professional can cause the external engagement thread 530 to threadably engage the body thread 522. At this point, the user can tip the delivery end 510 up and add a suitable lubricant, for example, saline into the delivery aperture 510 to lubricate the delivery end 510 and the implant prosthesis. The surgical professional can then orient the delivery end 510 either proximate to or partially or completely through the surgical incision. The surgical professional then begins to turn the handle portion 524, whereby the interaction of the external engagement thread 530 and the body thread 522 causes the engagement portion 528 to travel toward the delivery end 510. As the engagement portion 528 moves toward the delivery end 510, the sealing member 505 and implant prosthesis are similarly advanced toward the delivery end 510. Ultimately, the implant prosthesis is directed out the delivery aperture 512, through the surgical incision and into the surgical pocket. Due to the reduced diameter at the delivery end 510, the sealing member 505 and engagement portion 528 are prevented from reaching the delivery end 510 and the sealing member 505 cannot be inadvertently delivered out the delivery aperture 512. Due to the presence of the lubricant, the sealing member 505 is prevented from rotating with the engagement portion 528 and thus no rotation is imparted to the implant prosthesis as it is advanced toward and through the delivery end 510. By causing the rotatable plunger 504 to advance by rotation, the insertion process is slowed such that it can be controlled and the implant prosthesis is not subjected to high torque or stress that can damage the implant prosthesis. In some embodiments, the inner walls of one or more of the receiving end 506 and delivery end 510 can be coated with a hydrogel having high lubricity in the presence of saline. In an alternative embodiment, the delivery end 510 can comprise a replaceable component that is rotatably or insertably connected to the receiving end 506 to form the syringe body 502. In this way, the only portion of the implant prosthesis insertion device 500 that contacts the surgical incision can be quickly removed and replaced when the surgical procedure involves placement of two implant prosthesis in two different surgical pockets.

In another representative embodiment as shown in FIGS. 30A-30F, delivery sheet 50 can be configured such that a bottom edge 612 can more smoothly interface with a first lateral edge 614 and a second lateral edge 616 so as to define an arcuate portion 626 such that a sheet perimeter 628 defines a heart-like or stingray-like appearance. The bottom edge 612 can define an insertion tab 606 that projects outwardly form the bottom edge 612 so as to define a pair of intersections 630a, 630b. The bottom edge 612 can define a pair of arcuate lobe portions 632a, 632b that operably connect to and begin defining the first lateral edge 614 and second lateral edge 616. The first lateral edge 614 and second lateral edge 616 taper toward one another so as to define a folding tab 634.

Figure 30A:
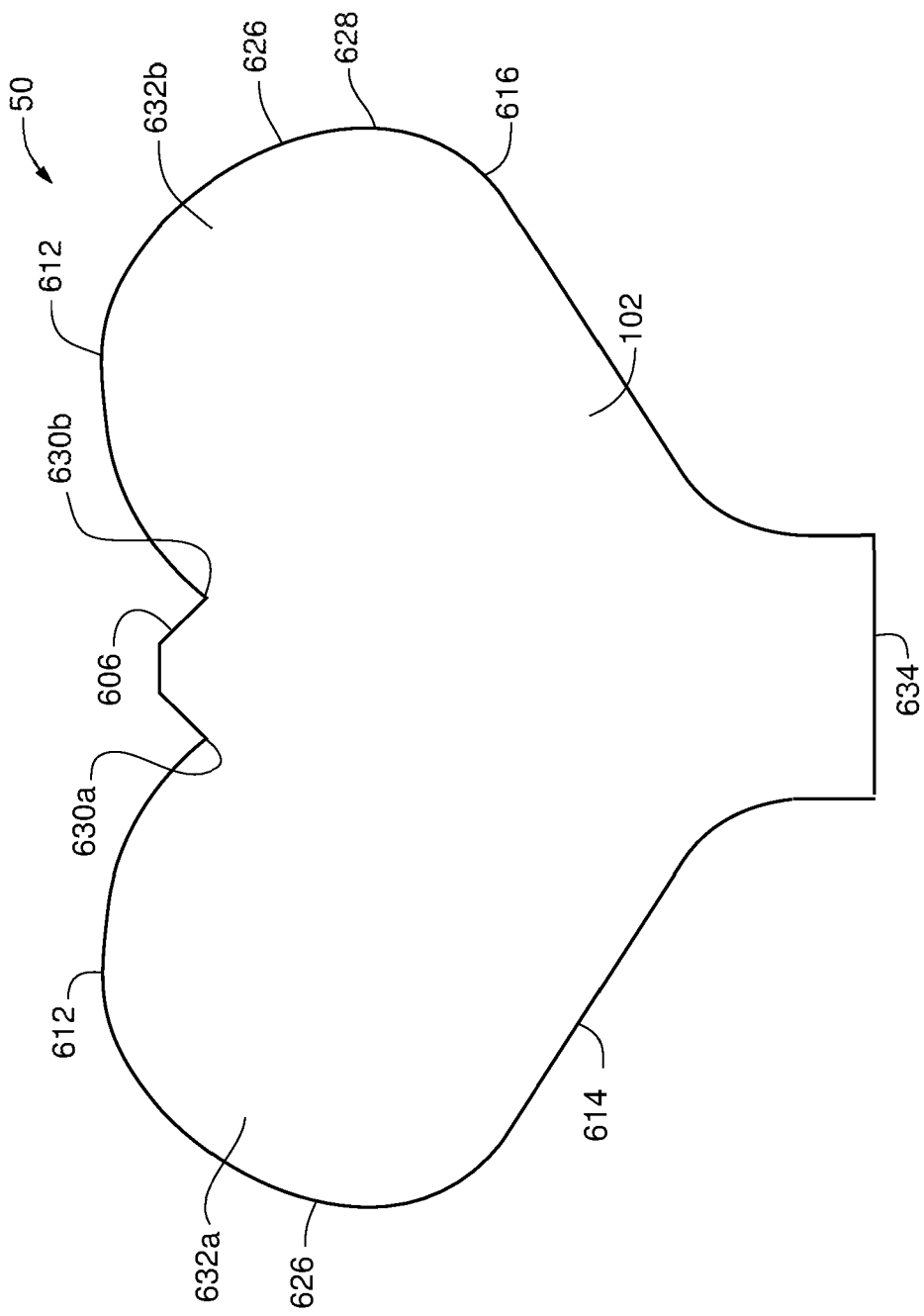
FIG. 30A is a top view of a delivery sheet according to another representative embodiment of the present invention.
Figure 30B:
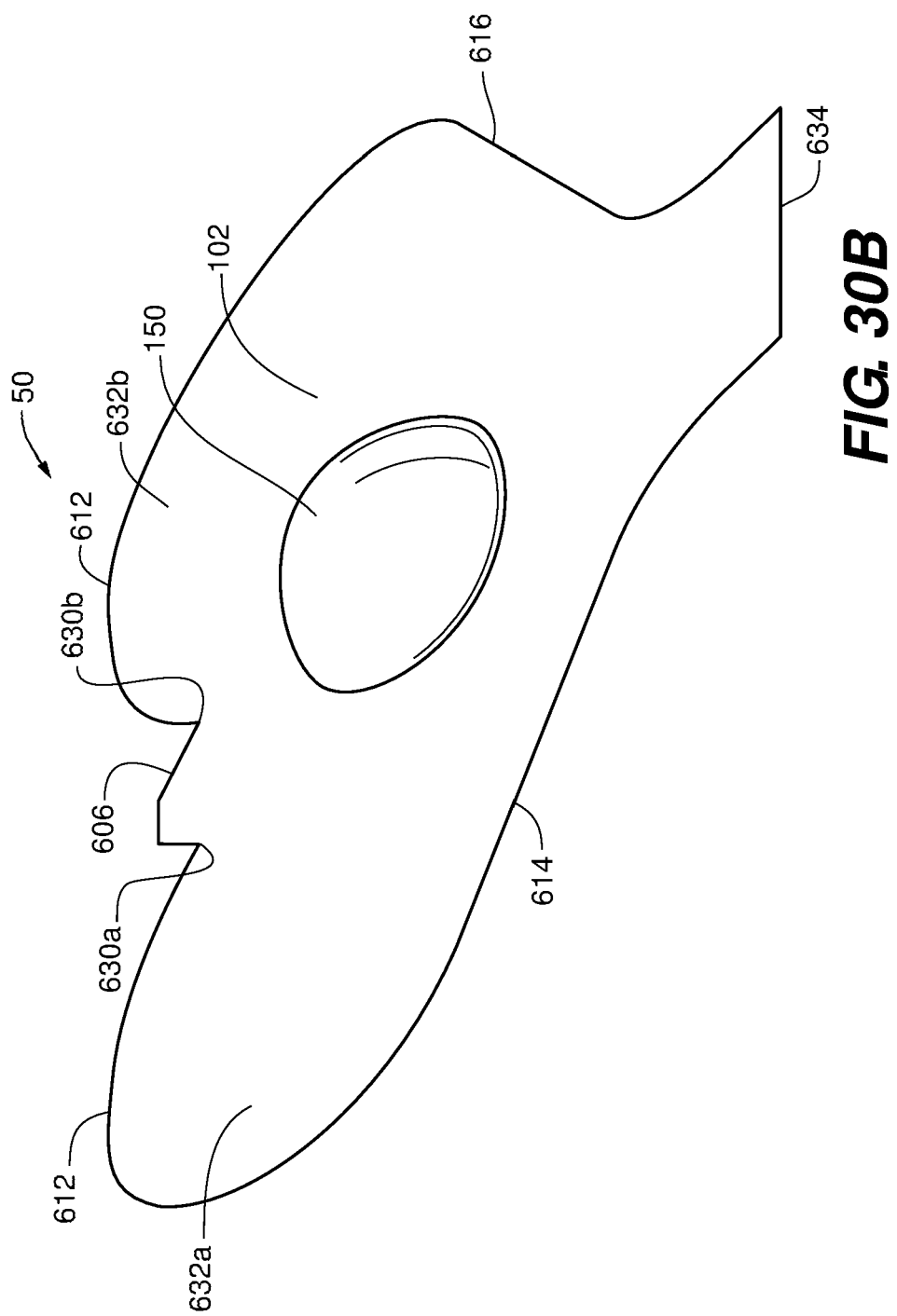
FIG. 30B is a perspective top view of the delivery sheet of FIG. 30 with an implant positioned on a first surface of the delivery sheet.
Figure 30C:
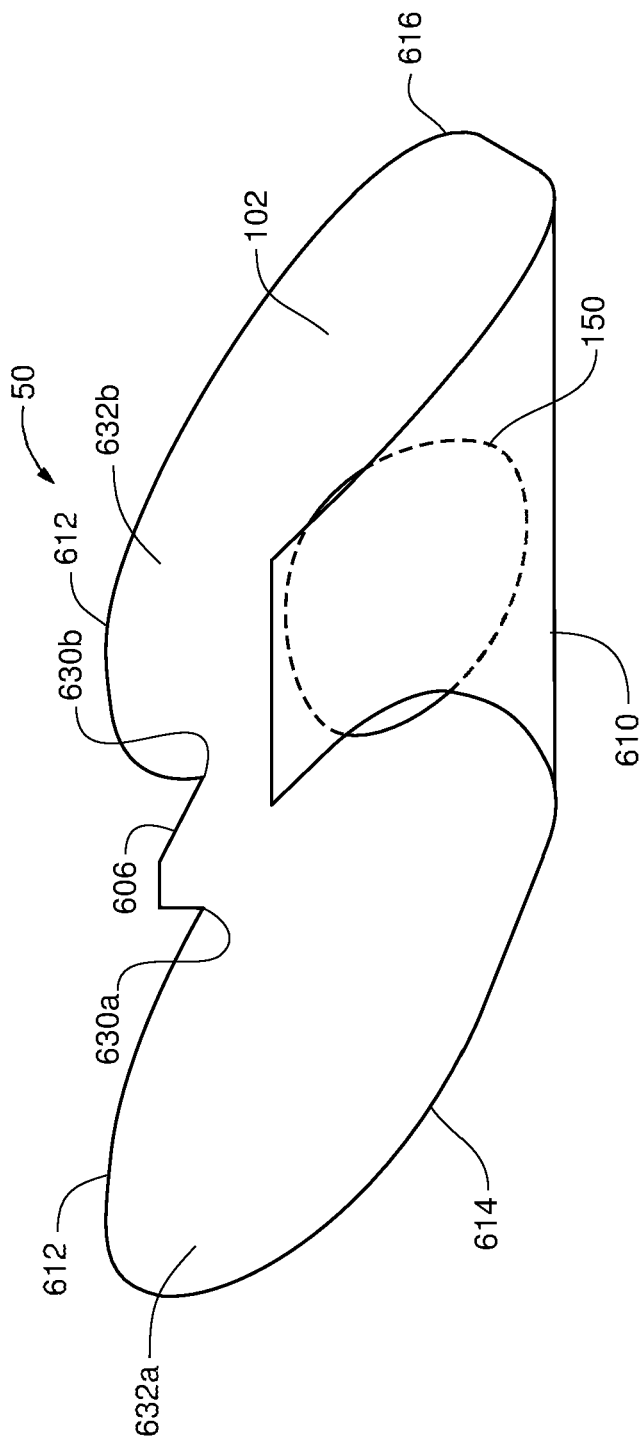
FIG. 30C is a perspective top view of the delivery sheet of FIG. 30B with a folding tab folded over the implant.
Figure 30D:
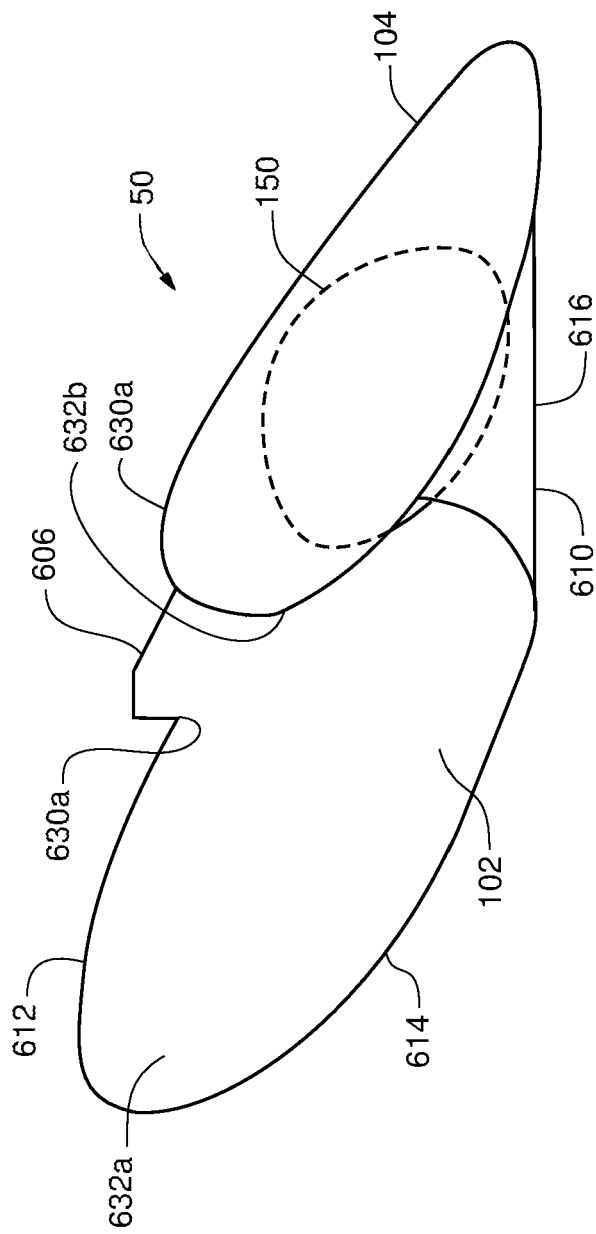
FIG. 30D is a perspective top view of the delivery sheet of FIG. 30C with a first lateral edge folded over the folding tab.
Figure 30E:
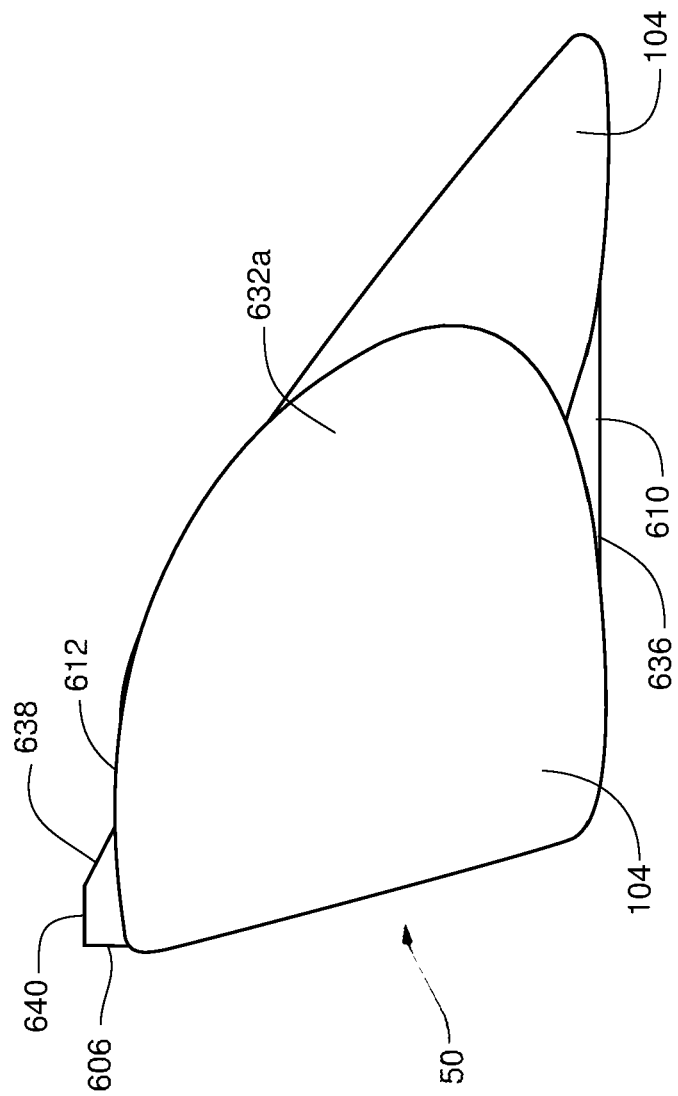
FIG. 30E is a perspective top view of the delivery sheet of FIG. 30D with a second lateral edge folded over the first lateral edge.

In a manner as similarly described with other embodiments of delivery sheet 50, operation and use of delivery sheet 50 can commence by positioning filled prostheses bladder or implant 150 on the first surface 102 as shown in FIG. 30B. As discussed previously with respect to related embodiments of delivery sheet 50, the method of use can further comprise the application of lubricants, either by activating lubricants already present on the first surface 102 by moistening the first surface 102 or by applying a conventional lubricant. A user can then manually fold the folding tab 634 toward the insertion tab 606 such that the folding tab 634 at least partially covers the implant 150 as shown in FIG. 30C. With the folding tab 634 folded in this fashion, a top edge 610 is defined between the first lateral edge 614 and the second lateral edge 616. Next, the user can fold the second lateral edge 616 and consequently, the arcuate lobe portion 632b toward the first lateral edge 614 and over the implant 150 as shown in FIG. 30D. Generally, the amount of the second lateral edge 616 and the arcuate portion 632b that is folded over the implant 150 is the amount of bottom edge 612 until the user reaches the intersection 630b, which provides an indication that enough of the second lateral edge 616 has been folded far enough over the implant 150. Next, the user can then fold the first lateral edge 614, and consequently the arcuate lobe portion 632a over the second lateral edge 616, the arcuate lobe portion 632b and the folding tab 634 so as to define a closed upper end 636 at the top edge 610 as shown in FIG. 30E. The amount of the first lateral edge 614 and the arcuate portion 632a that is folded over the implant 150 is the amount of bottom edge 612 until the user reaches the intersection 630a, which provides an indication that enough of the first lateral edge 614 has been folded far enough over the implant 150 to define the closed upper end 636. The user folds the second lateral edge 616 and a portion of the bottom edge 612 over the first lateral edge 614 until the user reaches the intersection 632b, which provides an indication that the second lateral edge 616 has been folded far enough over the first lateral edge 614 and the implant 150. At this point, the manipulation of the first lateral edge 614 and second lateral edge 616 has caused the bottom edge 612 to roll up, whereby the insertion tab 606 has been rolled to form a delivery nozzle 638 with an opening 640.

Figure 30F:
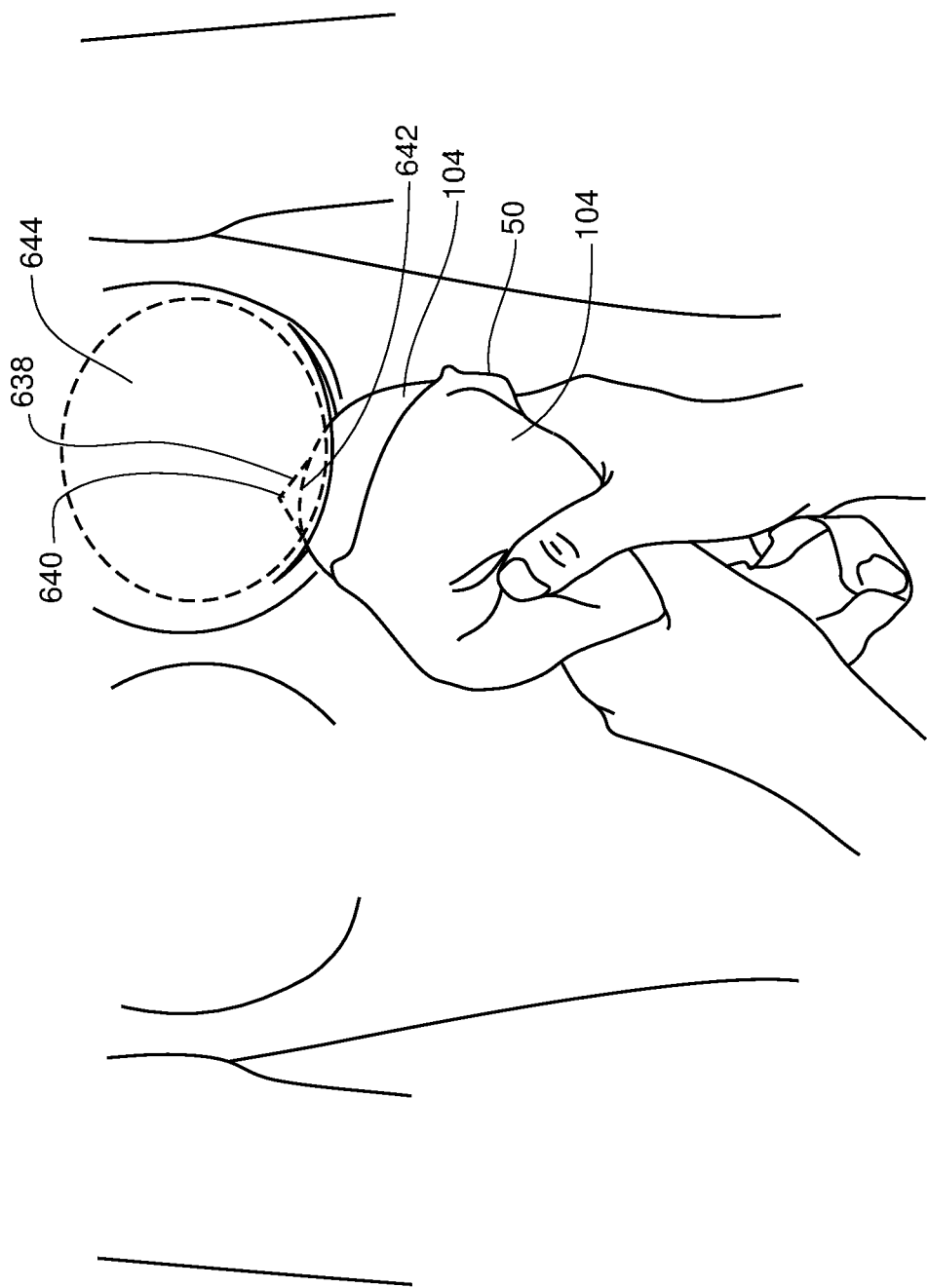
FIG. 30F is a top, partially hidden view of the delivery sheet delivering the implant though an incision and into a cavity within a female breast.

Next the user directs the insertion tab 606 into proximity with an incision 642 such that a portion of the delivery nozzle 638 is inserted through the incision 642 and the opening 640 is in communication with a surgical cavity 644, for example a surgical cavity within a female breast as shown in FIG. 30F. In one preferred embodiment, insertion tab 606 is fabricated from a more rigid plastic or polymer than surfaces 102 and 104 of delivery sheet 50 such that the pressure/tension from the incision 642 helps to maintain the rolled shape of the delivery nozzle 638 and consequently the folding of the first lateral edge 614, the second lateral edge 616 and the folding tab 634 such that the implant 150 is fully constrained. As this point, the user can being rolling/squeezing the delivery sheet 50 proximate the top edge 610 closed upper end 636 such that the implant 150 is directed toward the delivery nozzle 638. Due to the pliable nature of the implant 150, the implant 150 can be squeezed through the delivery nozzle 638 and opening 640 and into the surgical cavity 644 even though the implant 150 has a resting disposition or size that is larger than a diameter of the delivery nozzle 638 and opening 640. With the implant 150 placed in the surgical cavity 644, the user can remove the delivery nozzle 638 from the incision 642 and either repeat the process for a second implant 150 or simply discard the delivery sheet 50.

Figure 31A:
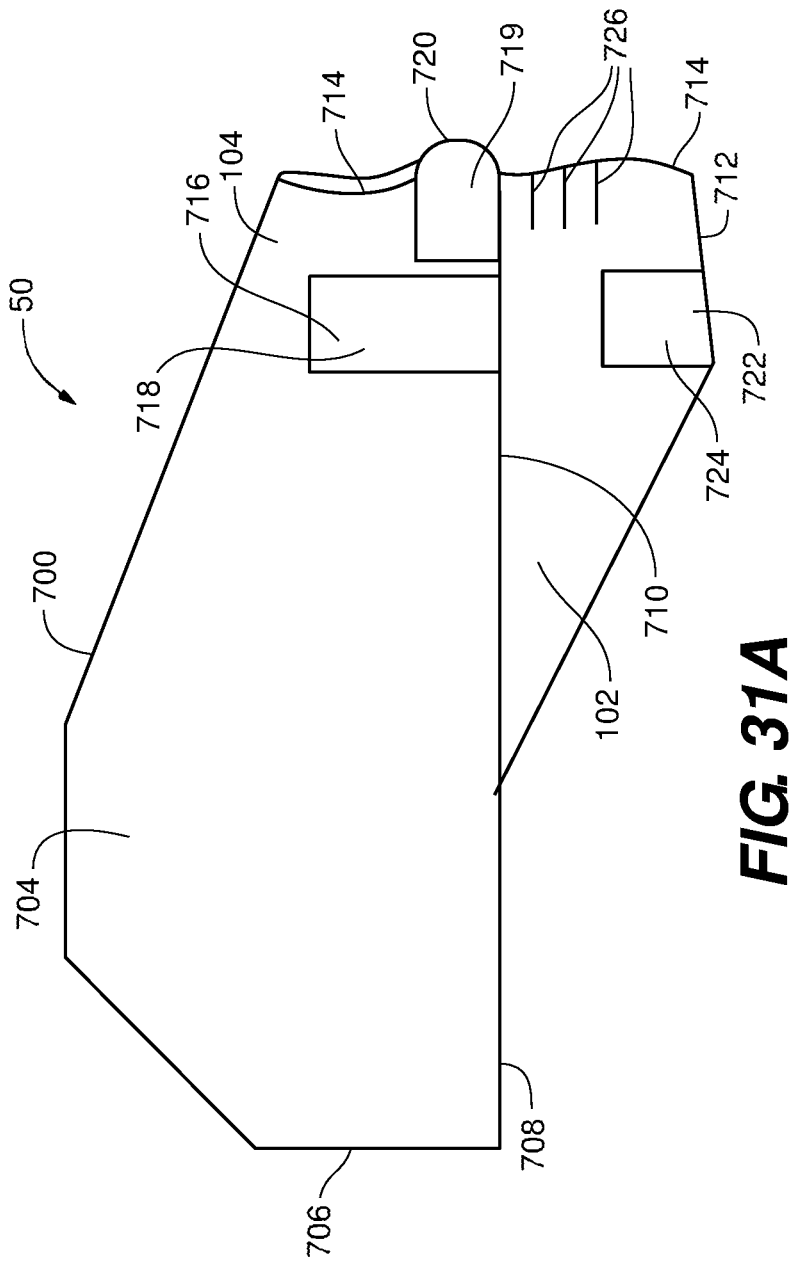
FIG. 31A is a top view of a delivery apparatus for delivering a filled prosthetic bladder according to another representative embodiment of the invention.
Figure 31B:
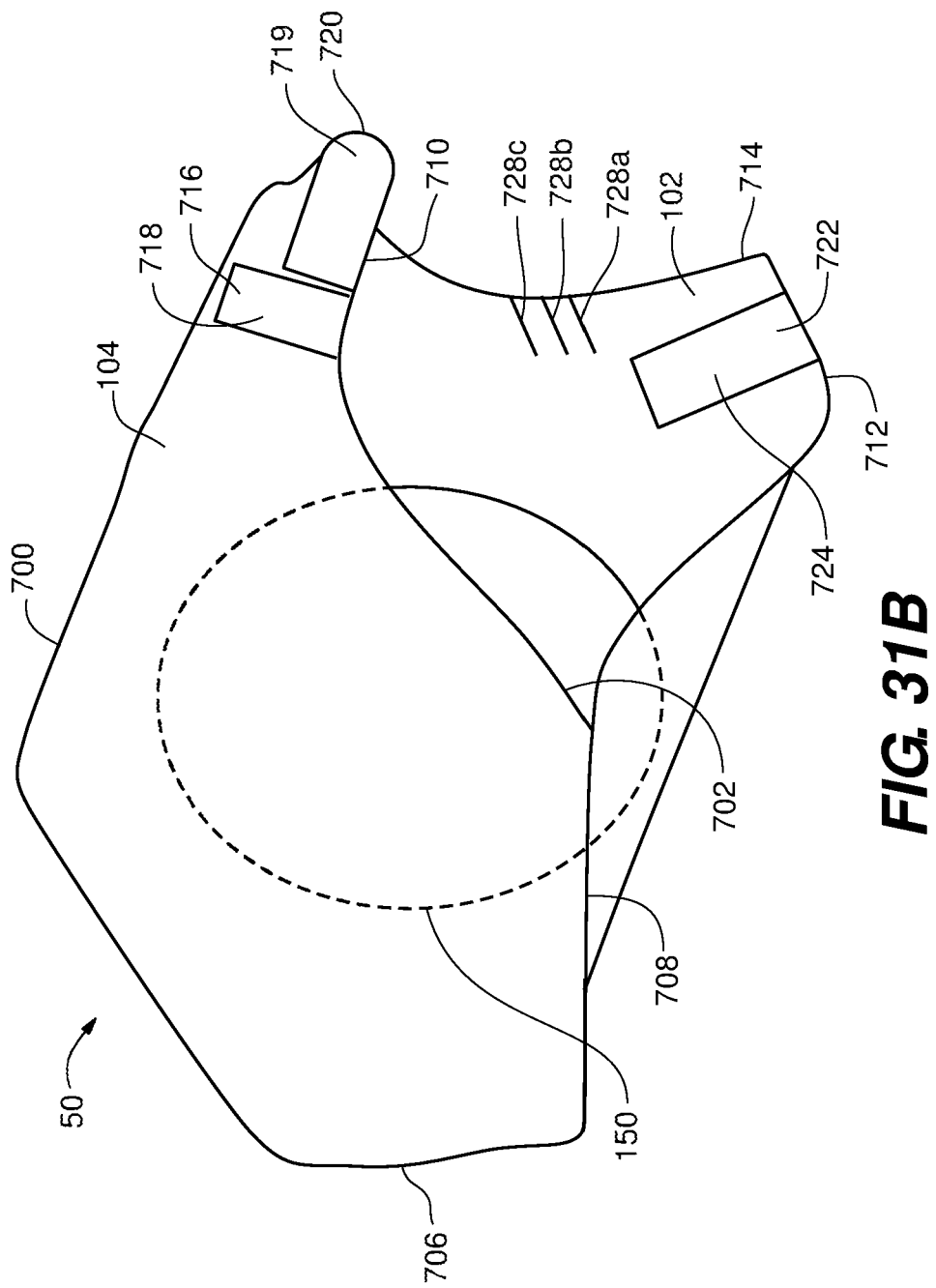
FIG. 31B is a partially hidden, top, perspective view of the delivery apparatus of FIG. 31A partially enclosing the filled prosthetic bladder.
Figure 31C:
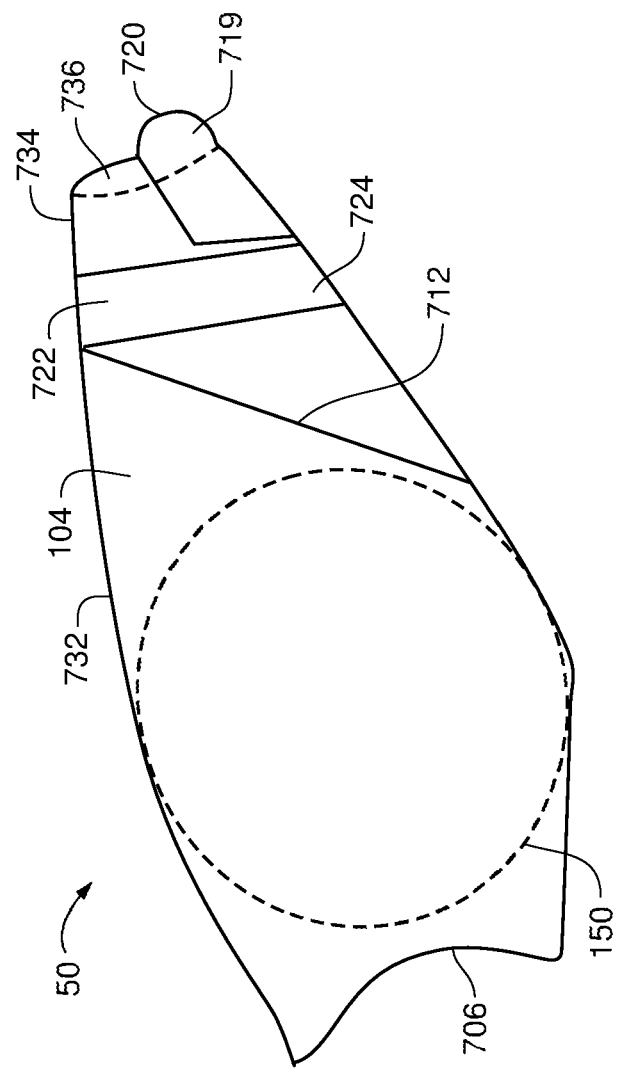
FIG. 31C is partially hidden, top view of the delivery apparatus of FIG. 31A configured for insertion of the filled prosthetic bladder in a surgical cavity.

In another representative embodiment as shown in FIGS. 31A-31C, delivery sheet 50 can be configured in an initially partially closed disposition 700 wherein the delivery sheet 50 has been formed such that first surface 102 defines an internal pocket 702 while the second surface 104 defines an external surface 704. As shown in FIGS. 31A and 31B, the internal pocket 702 is generally defined by a closed end 706 and a partially sealed lateral edge 708 where a first lateral edge 710 and a second lateral edge 712 are permanently joined. First lateral edge 710 can interface with a delivery edge 714 at a location distal to the closed end 706. First lateral edge 710 can include a first fastener strip 716, for example, a first hook and loop fastener strip 718 on the second surface 104. At the intersection of the first lateral edge 710 and delivery edge 714, an insertion tab 719 can be defined such that an insertion tip 720 extends beyond the deliver edge 714. The insertion tab 718 can be formed of a more rigid material than delivery sheet 50 to allow better control of the insertion tip 720 during use. Second lateral edge 712 can include a second fastener strip 722, for example, a second hook and loop fastener strip 724 on the first surface 102. Second lateral edge 712 also intersects with the delivery edge 714, whereby delivery edge 714 can comprise one or more visible indicia 726 on the inner surface 102 that are directly related use with implants 150 of varying size. For example, the visible indicia 726 can define fold or wrap guidelines corresponding to the volume of implant 150, for example, a largest implant wrap line 728a, a medium implant wrap line 728b and a smallest implant wrap line 728c. For purposes of clarification only, largest implant wrap line 728a can correspond to a 550 cc implant, medium implant wrap line 728b can correspond to a 450 cc implant and smallest implant wrap line can correspond to a 315 cc implant. These implant volumes are representative only and the implant volumes can be more or less than those disclosed and there can comprise more or less wrap lines than the three wrap lines presently disclose.

In use, the implant 150 can be inserted through an initial opening 730 defined by the first lateral edge 710, second lateral edge 712 and the delivery edge 714 such that the implant 150 is at least partially within the internal pocket 702 as shown in FIG. 31B. At this point, the first surface 102 can be moistened to activate a lubrication coating present on the first surface 102 or alternatively, a lubrication agent can be applied into the internal pocket 702. Next the user can begin to wrap the second lateral edge 712 over first lateral edge 710, whereby the first hook and loop fastener 718 and the second hook and loop fastener 724 can be operably connected and retained so as to define an insertion configuration 732 as shown in FIG. 31C. While the first and second fastener strips 716 and 722 are described as hook and loop fasteners, it will be understood that other suitable fasteners including, for example, adhesives, tapes, snaps and the like can be similarly employed without departing the scope of the present disclosure. As the user wraps the second lateral edge 712 over the first lateral edge 710, the user can align the appropriate wrap line with the first lateral edge 710 such that the insertion configuration 732 forms a delivery nozzle 734 having a delivery opening 736 that corresponds with the volume of the implant 150. The insertion tip 720 can then be directed through the incision 642 such that the delivery opening 736 is within the surgical cavity 644. The user can then begin squeezing or wrapping the external surface 704 proximate the closed end 706 direct the implant 150 toward and ultimately through the delivery nozzle 734 and into the surgical cavity 644. Due to the pliable nature of the implant 150, the implant 150 is able to be delivered though the delivery opening 736 even if the implant 150 has a resting size larger than the delivery opening 736. The combination of the joined first and second fastener strips 716, 722, the rigid insertion tab 718 and the pressure/tension applied by the incision 642 cooperate to maintain the integrity of the delivery nozzle 734 as the implant 150 is inserted into the surgical cavity 644.

The presently disclosed embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

The invention claimed is:
1. A delivery system for accessing a surgical cavity, comprising:

a sheet having a first surface and a second surface, the sheet defining a pair of lateral edges, a top edge and a bottom edge, wherein at least one of the lateral edges, the top edge and/or the bottom edge include a shaped memory feature, wherein said shaped memory feature is configured to wrap at least one of the lateral edges, the top edge and/or the bottom edge around a prosthesis placed on the first surface to initiate formation of an opening through which the prosthesis is introduced into a surgical cavity.

2. The delivery system of claim 1, wherein the prosthesis comprises a breast implant.

3. The delivery system of claim 1, wherein the first surface includes a lubricant.

4. The delivery system of claim 3, wherein the lubricant comprises an unactivated lubricant coating such that placement of the prosthesis on the first surface activates the unactivated lubricant coating.

5. The delivery system of claim 1, wherein the opening defines a delivery nozzle, wherein the delivery nozzle is positionable within the surgical cavity.

6. The delivery system of claim 2, wherein the shaped member feature is located on the bottom edge such that the bottom edge defines the delivery nozzle.

7. The delivery system of claim 1, wherein the sheet further comprises at least a pair of fastener strips on the sheet, wherein the fastener strips can be engaged to retain the sheet around the prosthesis.

8. The delivery system of claim 7, wherein the fasteners strips are proximate each lateral edge.

9. The delivery system of claim 7, wherein the fastener strips are positioned on one or both of the first and second surfaces.

10. The delivery system of claim 1, wherein the sheet further comprises at least three fastener strips on the sheet, wherein two of the fastener strips can be selectively engaged to retain the sheet around the prosthesis bases on a size or shape of the prosthesis.

11. The delivery system of claim 1, wherein the sheet comprises a multi-layer sheet such that the first surface and the second surface have different physical properties.

12. The delivery system of claim 1, wherein the sheet is configured to wrap about prostheses of various sizes and shapes.

13. The delivery system of claim 1, wherein the lateral edges are in a non-parallel orientation.

14. The delivery system of claim 1, wherein the top edge and the bottom edge are in a non-parallel orientation.

15. The delivery system of claim 1, wherein at least three of the pair of lateral edges, the top edge and the bottom edge are configured to wrap around the prosthesis placed on the first surface.

* * * * *